US008050486B2

(12) United States Patent
Walton

(10) Patent No.: US 8,050,486 B2
(45) Date of Patent: Nov. 1, 2011

(54) SYSTEM AND METHOD FOR IDENTIFYING A FEATURE OF A WORKPIECE

(75) Inventor: Steven R. Walton, Buckley, WA (US)

(73) Assignee: The Boeing Company, Chicago, IL (US)

( * ) Notice: Subject to any disclaimer, the term of this patent is extended or adjusted under 35 U.S.C. 154(b) by 1197 days.

(21) Appl. No.: 11/805,156

(22) Filed: May 22, 2007

(65) Prior Publication Data

US 2007/0271064 A1    Nov. 22, 2007

Related U.S. Application Data

(63) Continuation-in-part of application No. 11/383,681, filed on May 16, 2006, and a continuation-in-part of application No. 11/421,273, filed on May 31, 2006.

(51) Int. Cl.
G06K 9/00 (2006.01)
G01N 21/00 (2006.01)
G01B 11/30 (2006.01)

(52) U.S. Cl. ...... 382/141; 382/154; 356/606; 356/237.3

(58) Field of Classification Search .................. 382/141, 382/154; 356/603, 604, 606, 607, 610, 237.2, 356/237.3
See application file for complete search history.

(56) References Cited

U.S. PATENT DOCUMENTS

| 4,672,678 | A | 6/1987 | Koezuka et al. |
| 4,699,683 | A | 10/1987 | McCowin |
| 4,706,296 | A | 11/1987 | Pedotti et al. |
| 4,790,023 | A | 12/1988 | Matsui et al. |
| 4,975,863 | A | 12/1990 | Sistler et al. |
| 5,012,523 | A | 4/1991 | Kobayashi et al. |
| 5,032,211 | A | 7/1991 | Shinno et al. |
| 5,189,481 | A | 2/1993 | Jann et al. |
| 5,231,675 | A | 7/1993 | Sarr et al. |
| 5,562,788 | A | 10/1996 | Kitson et al. |

(Continued)

FOREIGN PATENT DOCUMENTS

EP    1072884 A2    1/2001

(Continued)

OTHER PUBLICATIONS

EP Communication Pursuant to Rule 62 EPC, Application No. EP 08251727, Sep. 10, 2008, European Patent Office (5 pgs).

(Continued)

*Primary Examiner* — Jon Chang
(74) *Attorney, Agent, or Firm* — Toler Law Group

(57) ABSTRACT

A feature of a workpiece can be identified. Two-dimensional data of at least a region of a workpiece and three-dimensional data of a portion of the region of the workpiece are acquired, such as by illuminating at least the region with at least a first light source disposed at a first angle of incidence relative to a plane of the region and illuminating the portion with a second light source, such as at least one laser, disposed at a second angle of incidence greater than the first angle of incidence. An estimated location of an attribute of a feature of the workpiece is determined from the three-dimensional data, and the feature is identified by analyzing the two-dimensional data in an area surrounding the estimated location of the attribute. Attributes of features can include without limitation a point along a line of an edge.

38 Claims, 18 Drawing Sheets

U.S. PATENT DOCUMENTS

| | | | |
|---|---|---|---|
| 5,703,784 | A | 12/1997 | Pearson |
| 5,742,504 | A | 4/1998 | Meyer et al. |
| 5,745,176 | A | 4/1998 | Lebens |
| 5,862,372 | A | 1/1999 | Morris et al. |
| 6,122,065 | A | 9/2000 | Gauthier et al. |
| 6,381,366 | B1 | 4/2002 | Taycher et al. |
| 6,408,429 | B1 | 6/2002 | Marrion, Jr. et al. |
| 6,723,951 | B1 | 4/2004 | McGraw |
| 6,744,913 | B1 | 6/2004 | Guest et al. |
| 6,799,619 | B2 | 10/2004 | Holmes et al. |
| 6,871,684 | B2 | 3/2005 | Engelbart et al. |
| 7,495,758 | B2 | 2/2009 | Walton |
| 7,590,442 | B2 * | 9/2009 | Boese et al. ............ 600/424 |
| 7,678,214 | B2 | 3/2010 | Engelbart et al. |
| 2002/0141632 | A1 | 10/2002 | Engelbart et al. |
| 2003/0102070 | A1 | 6/2003 | Black et al. |
| 2004/0060650 | A1 | 4/2004 | Holmes et al. |
| 2004/0257540 | A1 | 12/2004 | Roy et al. |
| 2005/0116952 | A1 | 6/2005 | Je et al. |
| 2006/0073309 | A1 | 4/2006 | Hogg |
| 2006/0108048 | A1 | 5/2006 | Engelbart et al. |
| 2007/0034313 | A1 | 2/2007 | Engelbart et al. |
| 2007/0097359 | A1 | 5/2007 | Engelbart et al. |
| 2007/0172129 | A1 * | 7/2007 | Tortora et al. ............ 382/218 |
| 2007/0277919 | A1 | 12/2007 | Savol |
| 2007/0280501 | A1 | 12/2007 | Walton |

FOREIGN PATENT DOCUMENTS

| | | |
|---|---|---|
| EP | 1334819 A1 | 8/2003 |
| EP | 1503206 A1 | 2/2005 |
| FR | 2188836 | 1/1974 |
| JP | 59060327 A | 4/1984 |
| JP | 8247736 | 9/1996 |
| JP | 2002-323454 | 11/2002 |
| WO | WO 99/00661 | 1/1999 |
| WO | WO 00-70303 | 11/2000 |
| WO | WO-00/70303 | 11/2000 |
| WO | WO 02/12870 | 2/2002 |
| WO | WO 02/29357 | 4/2002 |
| WO | WO 02-073173 A2 | 9/2002 |

OTHER PUBLICATIONS

Assembly Guidance Systems website at http://www.assemblyguide.com/HAMPI/Hampi.htm, "Automatic Ply Verification", 2 pages, printed Oct. 17, 2005.

UltraOptec, Inc. website at http://www.ultraoptec.com/luis-747/LUIS-747.html, "LUIS 747", 17 pages, printed Oct. 17, 2005.

Asla, M. Sa, Paulo Cezar Carvalho, and Luiz Velho; Recovering Registered Geometry and High Dynamic Range Texture with Coded Structure Light pp. 1-4. Printed from website http://www.wscg.zcu.cz/wscg2003/Papers_2003/E03.pdf. (2003).

Li Zhang; Brian Curless, and Steven Seitz, Department of Computer Science and Engineering, University of Washington; Rapid Shape Acquisition Using Color Structured Light and Multi-pass.Dynamic Programming; pp. 1-13; 13 pages printed from website http://www.grail.cs.washington.edu/projects/moscan/paper.pdf on Mar. 27, 2006.

Asla, M. Sa, Paulo Cezar Carvalho, and Luiz Velho; -BCSL: Structured Light Color Boundary Coding for 3D Photography; VMV 2002; pp. 1-9; Erlangen, Germany, Nov. 20-22, 2002. Printed from website http://www.visgraf.impa.br/Data/RefBib/PS_PDF/vmv02/bs-BCSL.pdf.

3D Images Using Color Structured Light; Way-2C Color Machine Vision—3D Images Using Color Structured Light; 2 pages printed from website http://www.way2c.com/w2csl.htm on Mar. 27, 2006.

U.S. Appl. No. 11/383,681, Final Office Action dated Apr. 14, 2011, (20 pgs).

U.S. Appl. No. 11/383,681, Non-Final Office Action dated Sep. 20, 2010, (15 pgs).

U.S. Appl. No. 11/383,681, Final Office Action dated Jun. 9, 2010, (12 pgs).

U.S. Appl. No. 11/383,681, Non-Final Office Action dated Jan. 28, 2010, (8 pgs).

Bennet et al., Experimental optical fan beam tomography; Applied Optics; vol. 23, No. 16; Aug. 15, 1984; (pp. 2678-2685).

Sharp et al., Material Selection/ Fabrication Issues for Thermoplastic Fiber Placement; Journal of Thermoplastic Composite Materials; vol. 8; Jan. 1995; (pp. 2-13).

Assembly Guidance Systems website at http://www.assemblyguide.com/HAMPI/Hampi.htm, Automatic Ply Verification, printed Oct. 17, 2005, (2 pgs).

UltraOptec, Inc. website at http://www.ultraoptec.com/luis-747/LUIS-747.html, "LUIS 747", printed Oct. 17, 2005, (17 pgs).

U.S. Appl. No. 11/421,273, Non-Final Office Action dated May 25, 2010, (22 pgs) .

U.S. Appl. No. 11/421,273, Final Office Action dated Mar. 4, 2010, (21 pgs).

U.S. Appl. No. 11/421,273, Non-Final Office Action dated Oct. 26, 2009, (22 pgs).

Malamas et al., A survey on industrial vision systems, applications and tools; Image and Vision Computing 21, 2003, (pp. 171-188).

Kim et al., Neural network-based inspection of solder joints using a circular illumination; Image and Vision Computing; vol. 13, No. 6, Aug. 1995, (12 pgs).

U.S. Appl. No. 11/421,273, Final Office Action dated Sep. 8, 2009, (23 pgs).

U.S. Appl. No. 11/421,273, Non-Final Office Action dated Apr. 16, 2009, (18 pgs).

Capson et al., A Tiered-Color Illumination Approach for Machine Inspection of Solder Joints, IEEE Transactions on Pattern Analysis and Machine Intelligence, vol. 10, No. 3, May 1988, (7 pgs).

International Search Report and Written Opinion for International Application No. PCT/US2007/012858, mailed Jan. 22, 2008, (14 pgs).

Paulson et al., Infrared Imaging Techniques for Flaw Detection in Composite Materials; Proceedings of the SPIE, Bellingham, Virginia, vol. 366, vol. 366, Aug. 26, 1982, (pgs. 88-95).

Asla et al., Recovering Registered Geometry and High Dynamic Range Texture with Coded Structure Light; printed from website—http://www.wscg.zcu.cz/wscg2003/Papers_2003/E03.pdf; 2003, (pgs. 1-4).

Zhang et al., Rapid Shape Acquisition Using Color Structured Light and Multi-pass Dynamic Programming; University of Washington, Dept. of Computer Science and Engineering, printed from website http://www.grail.cs.washington.edu/projects/moscan/paper.pdf on Mar. 27, 2006, (13 pgs).

Asla et al., -BCSL: Structured Light Color Boundary Coding for 3D Photography; VMV 2002, Erlangen, Germany, Nov. 2002, printed from website—http://www.visgraf.impa.br/Data/RefBib/PS_pdf/vmv02/bs-BCSL.pdf, (pgs. 1-9).

3D Images Using Color Structured Light; Way-2C Color Machine Vision, printed from website—http://www.way2c.com/w2csl.htm on Mar. 27, 2006, (2 pgs).

* cited by examiner

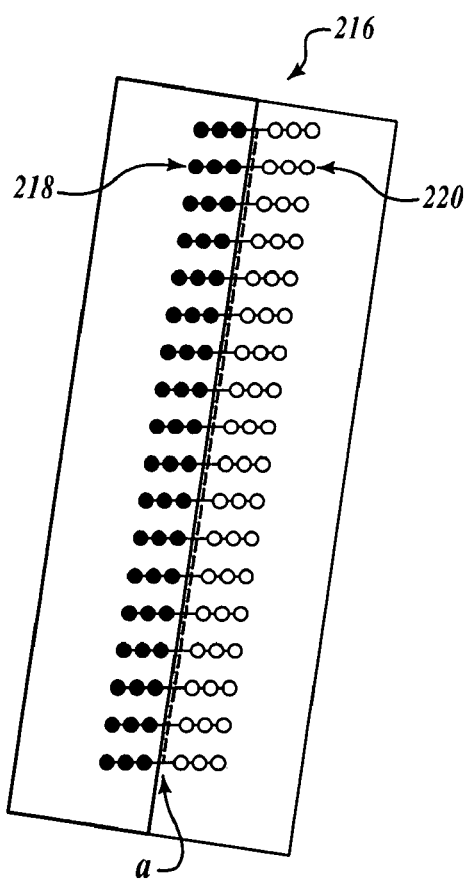 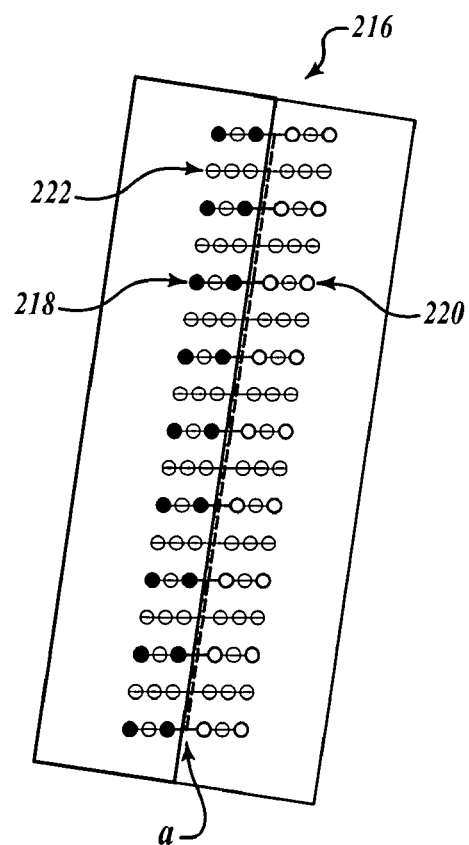
*FIG.18A*  *FIG.18B*

SYSTEM AND METHOD FOR IDENTIFYING A FEATURE OF A WORKPIECE

RELATED APPLICATIONS

This application is a Continuation-In-Part (CIP) application of U.S. patent application Ser. No. 11/383,681, filed May 16, 2006 and published as U.S. Patent Publication No. 2007/0277919, and U.S. patent application Ser. No. 11/421,273, filed May 31, 2006 and published as U.S. Patent Publication No. 2007/0280501, both of which are hereby incorporated by reference.

BACKGROUND

As part of a manufacturing process, a manufactured article or workpiece may be inspected for presence of defects or for compliance with a manufacturing specification or a design requirement or the like. For example, an inspection may be performed manually, such as by a human inspector with a microscope. Such manual inspection can be time- and labor-intensive. To that end, manual inspection of the workpiece can become a large part of the manufacturing process. Thus, such manual inspection may not be suitable for high-volume manufacturing processes.

Machine vision systems may be used to inspect a workpiece in order to increase inspection throughput over manual inspection by humans. Machine vision systems may analyze two-dimensional information and three-dimensional information to inspect a workpiece. As characterized by resolution, robustness, and speed of measurement, that which may be a strength of two-dimensional machine vision analysis conversely may be a weakness of three-dimensional machine vision analysis, and vice versa.

For example, two- and three-dimensional machine vision analysis of edge detection of a workpiece, such as a component made of composite tape or tow, will be considered. Regarding resolution, two-dimensional edge detection can produce an excellent average measurement of an edge line— because a large portion of an image frame is used; on the other hand, three-dimensional edge detection may be restricted to no more than the size of an image pixel and, therefore, can only locate one point. Regarding robustness, two-dimensional edge detection can be highly susceptible to image noise and surface artifacts that may resemble an edge; on the other hand, three-dimensional edge detection is not susceptible to image noise or surface artifacts at all. Regarding speed, two-dimensional edge detection may be slow—the two-dimensional edge detection algorithm must analyze an entire image before finding results; on the other hand, three-dimensional edge detection can be fast—the three-dimensional edge detection algorithm only has to analyze an image near a laser signature.

Therefore, a two-dimensional machine vision edge detection algorithm may perform well at determining precise location of an edge. However, the two-dimensional machine vision edge detection algorithm may be fooled by image noise and surface artifacts into finding "edges" that are not there. Moreover, analysis of an entire image by the two-dimensional machine vision edge detection algorithm may be time consuming. On the other hand, a three-dimensional machine vision algorithm can quickly detect a point without being susceptible to image noise or surface artifacts. However, the three-dimensional machine vision algorithm can only locate one point that is no more than the size of the image pixel.

Thus, neither two-dimensional machine vision analysis nor three-dimensional machine vision analysis is superior to the other in all three characteristics of resolution, robustness, and speed. However, two-dimensional machine vision analysis and three-dimensional machine vision analysis may be complementary to each other in the characteristics of resolution, robustness, and speed.

The foregoing examples of related art and limitations associated therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems and methods which are meant to be exemplary and illustrative, not limiting in scope. In various embodiments, one or more of the problems described above in the Background have been reduced or eliminated, while other embodiments are directed to other improvements.

According to exemplary embodiments, a feature of a workpiece can be identified. Two-dimensional data of at least a region of a workpiece is acquired, and three-dimensional data of a portion of the region of the workpiece is acquired. An estimated location of an attribute of a feature of the workpiece is determined from the three-dimensional data, and the feature is identified by analyzing the two-dimensional data in an area surrounding the estimated location of the attribute.

According to aspects, the feature can include an edge and the attribute can include a point along a line. Alternately, the feature can include a hole and the attribute can include points along a circle. Further, the feature can include a chamfered hole and the attribute can include points along two concentric circles.

According to other exemplary embodiments, a system for identifying a feature of a workpiece includes a first light source configured to illuminate at least a region of a workpiece and a second light source configured to illuminate a portion of the region of the workpiece. A sensor is configured to sense an image of the region and the portion of the region. A processor is operatively coupled to the sensor. The processor includes a first component configured to determine an estimated location of an attribute of a feature of the workpiece from three-dimensional data regarding the portion of the region of the workpiece and a second component configured to identify the feature by analyzing two-dimensional data regarding the region in an area surrounding the estimated location of the attribute.

According to aspects, the first light source may be disposed at a first angle of incidence relative to a plane of the region and the second light source may be disposed at a second angle of incidence relative to a plane of the region that is greater than the first angle of incidence. The first light source can include first and second lighting assemblies disposed towards ends of the region. The second light source can include one or more lasers. Further, the sensor can include a camera.

According to other exemplary embodiments, an edge can be detected. At least a region of a workpiece is illuminated with a pair of first light sources that are disposed at a first angle of incidence relative to a plane of the region and a portion of the region of the workpiece is illuminated with a second light source that is disposed at a second angle of incidence relative to a plane of the region that is greater than the first angle of incidence. A frame of information is captured. An estimated location of a point along a line defining an edge within the workpiece is determined from three-dimensional data from the frame of information, and location of the edge is refined by analyzing two-dimensional data from the frame of information in an area surrounding the estimated location of the point.

According to aspects, estimated locations of points along lines that define edges may be input into two-dimensional analysis. Candidate lines from the points may be formed at the estimated locations, and a median angle of the candidate lines can be determined. An angle of each candidate line can be compared with the median angle of the candidate lines, and a candidate line may be invalidated when its angle exceeds the median angle.

According to other exemplary embodiments, a location of a line can be refined. An estimated location of a point is inputted. A first search window centered around the estimated location of the point is generated. First and second edges of the first search window are each subdivided into edge points. All of the edge points along the first edge are connected with all of the edge points along the second edge to generate a first set of candidate lines, and which of the first set of candidate lines has a maximized power level is determined.

According to aspects, the length of the candidate line with maximized power level can be extended, and a second search window centered around the candidate line with maximized power level can be generated. First and second edges of the second search window each can be subdivided into edge points. All of the edge points along the first edge of the second search window can be connected with all of the edge points along the second edge of the second search window to generate a second set of candidate lines, and which of the second set of candidate lines has a maximized power level can be determined.

According to other exemplary embodiments, a head assembly can perform a manufacturing operation on a workpiece. The head assembly includes a tool moveable relative to a workpiece and configured to perform a manufacturing operation on a workpiece, and a monitoring unit is operatively coupled to and moveable with the tool relative to the workpiece. The monitoring unit includes first and second lighting assemblies disposed towards first and second sides of the monitoring unit, respectively, and the first and second lighting assemblies are configured to illuminate at least a region of the workpiece. A laser assembly is configured to illuminate a portion of the region of the workpiece upon which the tool has performed the manufacturing operation. A sensor is configured to sense an image of the region and the portion of the region, and a processor is operatively coupled to the sensor. The processor includes a first component configured to determine an estimated location of an attribute of a feature of the workpiece from three-dimensional data regarding the portion of the region of the workpiece and a second component configured to identify the feature by analyzing two-dimensional data regarding the region in an area surrounding the estimated location of the attribute.

According to aspects, the tool may be configured to perform an application of a composite tape onto the workpiece, and the monitoring unit may be configured to illuminate at least a region of the composite tape. The tool may include a spindle configured to support a supply of the composite tape, and a feed assembly may be configured to feed the composite tape from the supply to the workpiece, the feed assembly having a rotatable compaction roller configured to apply the composite tape onto the workpiece.

According to other exemplary embodiments, a system can perform a manufacturing operation on a workpiece. The system includes at least one head assembly configured to perform a manufacturing operation on a workpiece. The head assembly includes a tool moveable relative to a workpiece and configured to perform a manufacturing operation on a workpiece, and a monitoring unit operatively coupled to and moveable with the tool relative to the workpiece. The monitoring unit includes first and second lighting assemblies disposed towards first and second sides of the monitoring unit, respectively, and the first and second lighting assemblies are configured to illuminate at least a region of the workpiece. A laser assembly is configured to illuminate a portion of the region of the workpiece upon which the tool has performed the manufacturing operation, and a sensor is configured to sense an image of the region and the portion of the region. A processor is operatively coupled to the sensor. The processor includes a first component configured to determine an estimated location of an attribute of a feature of the workpiece from three-dimensional data regarding the portion of the region of the workpiece, and a second component configured to identify the feature by analyzing two-dimensional data regarding the region in an area surrounding the estimated location of the attribute. A translation platform is coupled to the head assembly. The translation platform is configured to operatively position the head assembly proximate the workpiece and to systematically move the head assembly along a translation path proximate the workpiece.

According to aspects, the tool may be configured to perform an application of a composite tape onto the workpiece, and the monitoring unit may be configured to illuminate at least a region of the composite tape. The tool may include a spindle configured to support a supply of the composite tape, and a feed assembly configured to feed the composite tape from the supply to the workpiece, the feed assembly having a rotatable compaction roller configured to apply the composite tape onto the workpiece.

In addition to the exemplary embodiments and aspects described above, further embodiments and aspects will become apparent by reference to the drawings and by study of the following detailed description.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIGS. 18A and 18B illustrate exemplary filtering of candidate lines; and

DETAILED DESCRIPTION

Given by way of overview, a feature of a workpiece can be identified. Two-dimensional data of at least a region of a workpiece and three-dimensional data of a portion of the region of the workpiece are acquired, such as by illuminating at least the region with at least a first light source disposed at a first angle of incidence relative to a plane of the region and illuminating the portion with a second light source, such as at least one laser, disposed at a second angle of incidence greater than the first angle of incidence. An estimated location of an attribute of a feature of the workpiece is determined from the three-dimensional data, and the feature is identified by analyzing the two-dimensional data in an area surrounding the estimated location of the attribute. Attributes of features can include without limitation a point along a line of an edge.

Details of several non-limiting, exemplary embodiments will be set forth below. First, an overview of exemplary embodiments and system components will be set forth. Next, an exemplary embodiment for monitoring automated composite fabrication processes will be explained. Then, exemplary embodiments for identifying features in a workpiece will be explained.

Overview of Exemplary Embodiments and System Components

Figure 1:
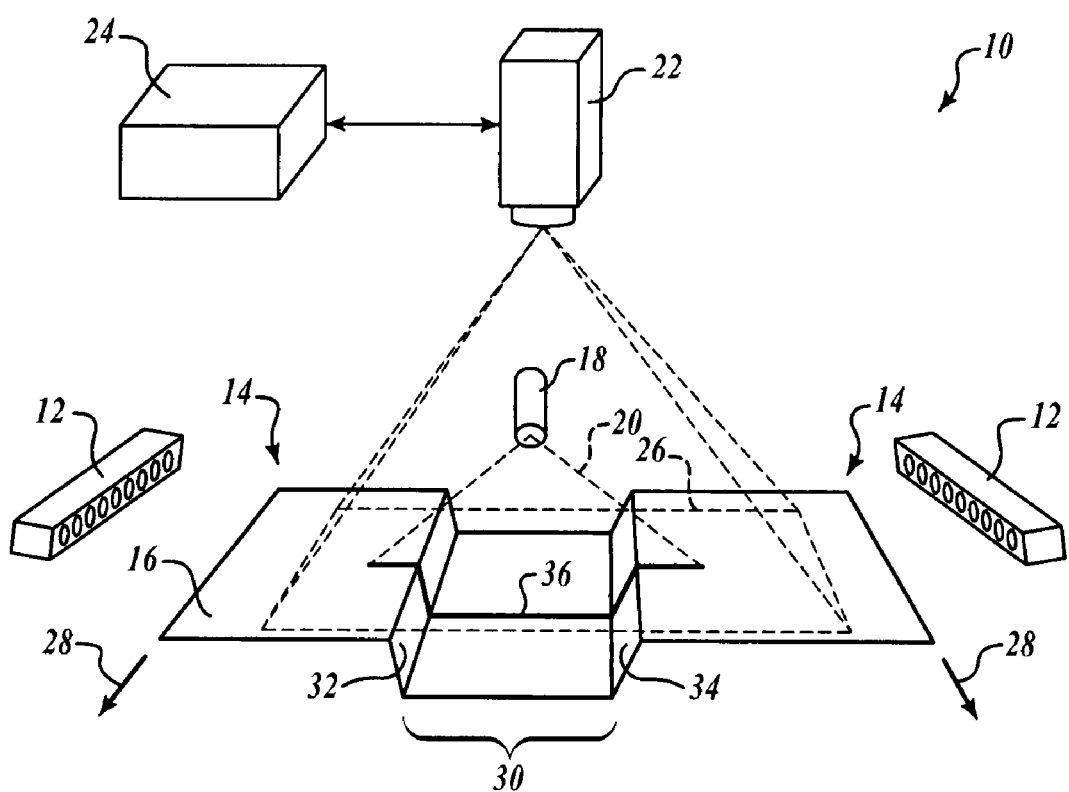
FIG. 1 is a perspective view of an exemplary system for identifying a feature of a workpiece according to an embodiment.

Referring to FIG. 1, an exemplary system 10 can identify a feature of a workpiece. Given by way of non-limiting example, the system 10 is well suited to detect and measure edges of a gap or overlap between components of a workpiece. Given by way of non-limiting example, the system 10 may be employed to detect and measure a gap or overlap between edges of composite tape or tow. However, the system 10 is not limited to use in detecting and measuring a gap or overlap between edges of composite tape or tow. Given by way of further non-limiting examples, as will be discussed below, the system 10 can be used to detect and measure location and size of a hole in a workpiece or a chamfer in a hole in a workpiece.

Thus, in some embodiments the system 10 can identify, that is detect and measure, an attribute of a feature of a workpiece. To that end, the feature can include an edge and the attribute can include a point along a line. Also, the feature can include a hole and the attribute can include points along a circle. Further, the feature can include a chamfered hole and the attribute can include a plurality of points along two concentric circles. While the system 10 is not limited to identification of such attributes of such features, for the sake of brevity these attributes and features listed above will provide the examples for explanation of non-limiting, exemplary embodiments disclosed herein.

Embodiments of the system 10 can detect other features, as well. It will be understood that the term "feature," as used herein, is not meant to be limiting, as a feature could be any aspect, discontinuity, imperfection, defect, or flaw in the workpiece that may require attention by a technician, such as for repair or replacement of the workpiece or a portion of the workpiece. For example, a flaw could be a material wrinkle or foreign object debris ("FOD"), such as paper, plastic sheet, resin balls, carbon fiber "fuzzballs", or other material inimical to the production of composite parts. Moreover, embodiments of the system 10 can detect the presence of features associated with the workpiece that would not ordinarily be characterized as a "flaw", such as a ply boundary, topology, shape/contour, or a tape edge gap or overlap, the positioning of which are requirements of the engineered workpiece design specification.

Embodiments of the system 10 could be used to inspect any number of workpieces in a variety of industries where detection of features of the workpiece is required or desired, such as in the aircraft, automotive, or construction industries. Thus, the term "workpiece" is also not meant to be limiting, as the system 10 could be used to inspect any number of parts or structures of different shapes and sizes, such as machined forgings, castings, or panels. For instance, the inspection could be performed on newly manufactured workpieces or existing workpieces that are being inspected for preventive maintenance purposes. Further, the workpiece could be any number of composite, plastic, and/or metallic materials.

Still by way of overview and still referring to FIG. 1, in an exemplary embodiment the system 10 includes light sources 12 configured to illuminate at least a region 14 of a workpiece 16 and a light source 18 configured to illuminate a portion 20 of the region 14. A sensor 22 is configured to sense an image of the region 14 and the portion 20. A data processing system 24 is operatively coupled to the sensor 22. In some embodiments, the data processing system 24 can include a first component configured to determine an estimated location of an attribute of a feature of the workpiece 16 from three-dimensional data regarding the portion 20 and a second component configured to identify the feature by analyzing two-dimensional data regarding the region 14 in an area surrounding the estimated location of the attribute.

Still by way of overview, in an embodiment the sensor 22 looks down with a field-of-view 26 upon the workpiece 16, such as without limitation composite material, moving past in a direction indicated by arrows 28. The light sources 12 illuminate the region 14 with shallow incidence-angle light laterally from both sides of the workpiece 16. A gap 30 between edges of components of the workpiece 16, such as composite tape or tows, reflects off edges 32 and 34 from the light sources 12. The light source 18, such as a laser, projects a laser fan beam line across the gap 30. Information from the sensor 22 is provided to the data processing system 24 to produce frame information. Information regarding exemplary components of the system 10 is discussed in U.S. patent application Ser. No. 11/421,273, filed May 31, 2006 and published as U.S. Patent Publication No. 2007/0280501, the contents of which are hereby incorporated by reference.

In some embodiments, as discussed above the frame information can be used to detect an aspect, potential discontinuity, potential imperfection, potential defect, or potential flaw in the workpiece 16 that may require attention by a technician, such as for repair or replacement of the workpiece 16 or a portion of the workpiece 16, or features associated with the workpiece 16 that would not ordinarily be characterized as a "flaw". Such use of the frame information is set forth in U.S. patent application Ser. No. 11/421,273, filed May 31, 2006 and published as U.S. Patent Publication No. 2007/0280501, the contents of which are hereby incorporated by reference. In such cases, any potential flaws in the material can be detected during the fabrication process, such as the layup process. Thus, the process may be stopped and any potential flaws fixed or other actions taken as desired, thereby helping to prevent any flaws from being included in a final part or product.

In other embodiments, the frame information can be used to identify, that is detect and measure, an attribute of a feature of a workpiece. Two-dimensional data of the region 14 and three-dimensional data of the portion 20 are acquired by illuminating the region 14 with the light sources 12 and illuminating the portion 20 with the light source 18, and capturing a frame of information with the sensor 22. The frame of information is provided to the data processing system 24. An estimated location of an attribute of a feature of the workpiece 16 is determined from the three-dimensional data, and the feature is identified by analyzing the two-dimensional data in an area surrounding the estimated location of the attribute. This exemplary use of the frame information will be explained in detail further below.

Details will now be set forth regarding exemplary components of the system 10.

The light sources 12 illuminate the region 14 with shallow incidence-angle light laterally from both sides of the workpiece 16. Light from the light sources 12 is cast upon the workpiece 16 at a shallow angle of incidence relative to a plane of the workpiece to accentuate edges of components in the workpiece 16, such as composite tape or tows and to cast a shadow into any gap 30 or from any flaw, such as FOD, that may be present in the workpiece 16. According to embodiments, the incidence angle is shallow—for example, less than about 30°. The pitch or roll angle of the light sources 12 could be varied to change the incidence angle of a respective illumination beam on the workpiece 16. Thus, a range of incidence angles from approximately 5° to approximately 30° may be employed in order to match desired measurement accuracy of tape laps and gaps to the desired vertical depth of field of the embodiment, and to generate more data indicative of surface debris in order to separate actual tape edges from common ridge-like structures in central regions of the workpiece 16.

Each light source 12 is generally an arrangement of bulbs for generating a light wash, such as a beam of light or other structured light that is configured to illuminate a specific feature on the workpiece 16. Within the non-limiting context of a gap between composite tape or tows, the central portion of any given joint gap will tend to be darker than the surface, and a brighter glint along the top of the edges is produced. Thus, the two sides of a given joint may be differentiated because of the horizontal order of light and dark lines. Each light source 12 is capable of illuminating the workpiece 16 with structured light having a respective color (such as red, blue, green, white, or the like) or additional specific spectral content. The light sources 12 may include an array of light emitting diodes (LEDs), incandescent lamps, fluorescent lamps, or any other light source as desired. Additionally, the light sources 12 may be of a specific shape to enhance particular features present in the workpiece 16. Both of the light sources 12 may emit light of the same color.

Alternately, one of the light sources 12 may emit light of one color, such as without limitation blue light, and the other light source 12 may emit light of another color, such as without limitation green light. Emitting light of one color from one of the light sources 12 and light of another color from the other light source 12 can help accentuate any gaps 30 in the workpiece 16, such as a gap between composite tape or tows. For example, the edge 32 on one side of the gap 30 may be illuminated with one color, such as without limitation blue light, from one of the light sources 12 and the edge 34 on the other side of the gap 30 may be illuminated with another color, such as without limitation green light, from the other light source 12.

The light source 18 suitably includes a laser generator capable of illuminating the workpiece 16 with a fan beam, thereby projecting a laser fan beam line across the gap 30. The fan beam is generally a beam of light that spans outwardly in a plane from its origin location. A planar fan beam may be oriented by rotating around its optical axis such that the fan produces a signature line on the workpiece 16 substantially perpendicular to the optical axis of the laser generator, in the plane perpendicular to the workpiece 16 described by the incidence angle of the laser generator, or at any angle in between. Thus, a laser generator used as the light source 12 could be a laser projector, a laser scanner, or the like capable of illuminating the workpiece 16 with a fan beam. The pitch or roll angle of the light source 18 could be varied to change the incidence angle of a respective illumination beam on the workpiece 16. The signature line from the light source 18 suitably is a different color from the color (or colors) of the light sources 12. Typically, the signature line from the light source 18 may be a red line and, as a result, the light sources 12 typically may emit any one or a combination of white light, blue light, green light, or the like.

The light sources 12 and 18 work together as follows, as explained in the non-limiting context of illumination of gaps between composite tows. The light sources 12 are positioned to generate linear light washes that are generally parallel to the direction of movement of the workpiece 16, indicated by the arrows 28, and substantially parallel to the edges of gaps, while the light source 18, such as a laser generator, is positioned to generate a fan beam generally perpendicular to the direction of movement of the workpiece 16. The light sources 12 are thus configured to illuminate the respective edges 32 and 34 of the gap 30, while the light source 18 is capable of generating a fan beam configured as a signature line 36 on the workpiece 16, thereby highlighting the gap 30 by the mechanism of a "step" in the laser line 36 as seen by the sensor 22. Each of the pair of light sources 12 illuminates a respective edge 32 and 34 on an opposite side of the gap 30, perpendicular to the light source 18. Therefore, as mentioned above, the opposing edges 32 and 34 of the gap 30 may be differentiated when the pair of light sources 12 and the light source 18 utilize colors that can be differentiated from one another.

The sensor 22 is any suitable camera or other image capturing device capable of capturing data indicative of the workpiece 16 such that the data processing system 24 can process the data and determine whether a flaw is present and/or provide information, such as attributes, indicative of various features of the workpiece 16. In particular, the sensor 22 typically captures images of the workpiece 16, and the data processing system 24 processes the images. The sensor 22 is positioned to capture images generally perpendicular to the workpiece 16, although the sensor 22 could be located at other positions and/or orientations if desired, such as in instances in which the surface of the workpiece 16 is non-planar or where a particular feature desired to be detected is best imaged with a particular orientation of the sensor 22. The system 10 may include one or more sensors 22, such as without limitation a respective sensor 22 for each tape laying head when used in such a setting.

The sensor 22 may be a commercially available camera capable of acquiring monochrome images or color images, not necessarily limited to the visible spectrum of light. While use of a color camera can permit enhanced detection of shadows created by light sources 12 of different colors as (as discussed above), one or more tradeoffs over use of a monochrome camera may be involved, such as any one or more of longer exposure times, increased bandwidth, decreased resolution, and/or increased processing power. Given by way of non-limiting example, in one embodiment, the sensor 22 may be a television or other type of video camera, an infrared-sensitive camera, a visible light camera with infrared-pass filtration, a fiber optic camera, a coaxial camera, Charge Coupled Device (CCD), or Complementary Metal Oxide Sensor (CMOS). The sensor 22 may also include filter systems or other features by which one or more specific frequencies of light are recorded. The sensor 22 can be positioned proximate the workpiece 16 on a stand or mounted to a frame or similar device. For instance and as will be discussed further below, the sensor 22 could be carried proximate to a tape laying head on a lamination machine and translate along with a gantry.

In some embodiments, the data processing system 24 may include a display device (not shown in FIG. 1) that is configured to display images representing data captured by the sensor 22 in real time such that a real-time video display of the captured data may be shown. Also, in some embodiments, the data processing system 24 may be configured to allow a user to capture one or more still images of the data and, for example, to display the still images on a display device or print the images. However, it should also be understood that the sensor 22 may be adapted to capture images at pre-determined times and then to send the images to the data processing system 24 for display by a graphical interface or for output by an output device, such as a printer.

It will be further understood that each sensor 22 may include an associated data processing system 24, while each data processing system 24 may, in turn, be in communication with a central data system (not shown in FIG. 1). Thus, a central data system in such a tiered or networked architecture could collect and/or further analyze images captured by respective sensors 22 and/or images or other data provided by respective data processing systems 24.

In addition, the data processing system 24 includes a computer processor, one or more computer processing components, or other computing device or devices that may be adapted to execute one or more applications (that is, computer software programs) and to otherwise operate under control of a standard operating system. For instance, the data processing system 24 may employ various computer software programs for processing and displaying the images captured by the sensor 22. As will be explained in further detail below, the data processing system 24 and, more particularly, the software programs executed by the data system can employ various algorithms for analyzing and interpreting the images captured by the sensor 22. Typically, the operating system and the various applications, that is computer software programs, are stored in a memory device or are otherwise accessible to the processor or other computing device. Construction and operation of computer processors is well known, and a detailed discussion of construction and operation of computer processors is not required for an understanding of embodiments.

Now that an overview of the system 10 and its components has been set forth, an exemplary application will be explained by way of non-limiting example.

Exemplary Embodiment for Monitoring Automated Composite Fabrication Processes

Embodiments of the system 10 could be used during the assembly or processing of the workpiece 16 (such as without limitation as composite tape is being laid upon a mandrel), as well as before or after assembly for providing information characteristic of the workpiece. For example, the system 10 could be utilized during the manufacture of aircraft wing skins or stringers, such as in conjunction with a lamination machine for laying onto a workpiece composite tape (typically 0.5" or wider material) or tow (typically less than 0.5" in width) plies of varying shapes. Differing width material may be applied to a given ply, depending upon engineering requirements. A lamination machine, as known to those skilled in the art, is a device for laying this resin-impregnated carbon fiber material onto a mandrel to form a workpiece and can have various configurations. For instance, the lamination machine could include a gantry and a plurality of tape heads for laying down tape of composite material. The gantry is capable of translating so that tape is laid as the mandrel rotates and as the gantry translates longitudinally. However, although the system 10 is discussed herein in conjunction with a lamination machine for laying composite tape or tow plies onto a workpiece, the system 10 could be employed to inspect various workpieces during various processes. For example, the system 10 can be mounted onto a moving lamination head, a separate moving gantry, or statically on any portion of the machine that has appropriate access to the workpiece 16, and may be enabled, disabled, or dynamically reconfigured according to the requirements of a particular manufacturing process.

Figure 2:
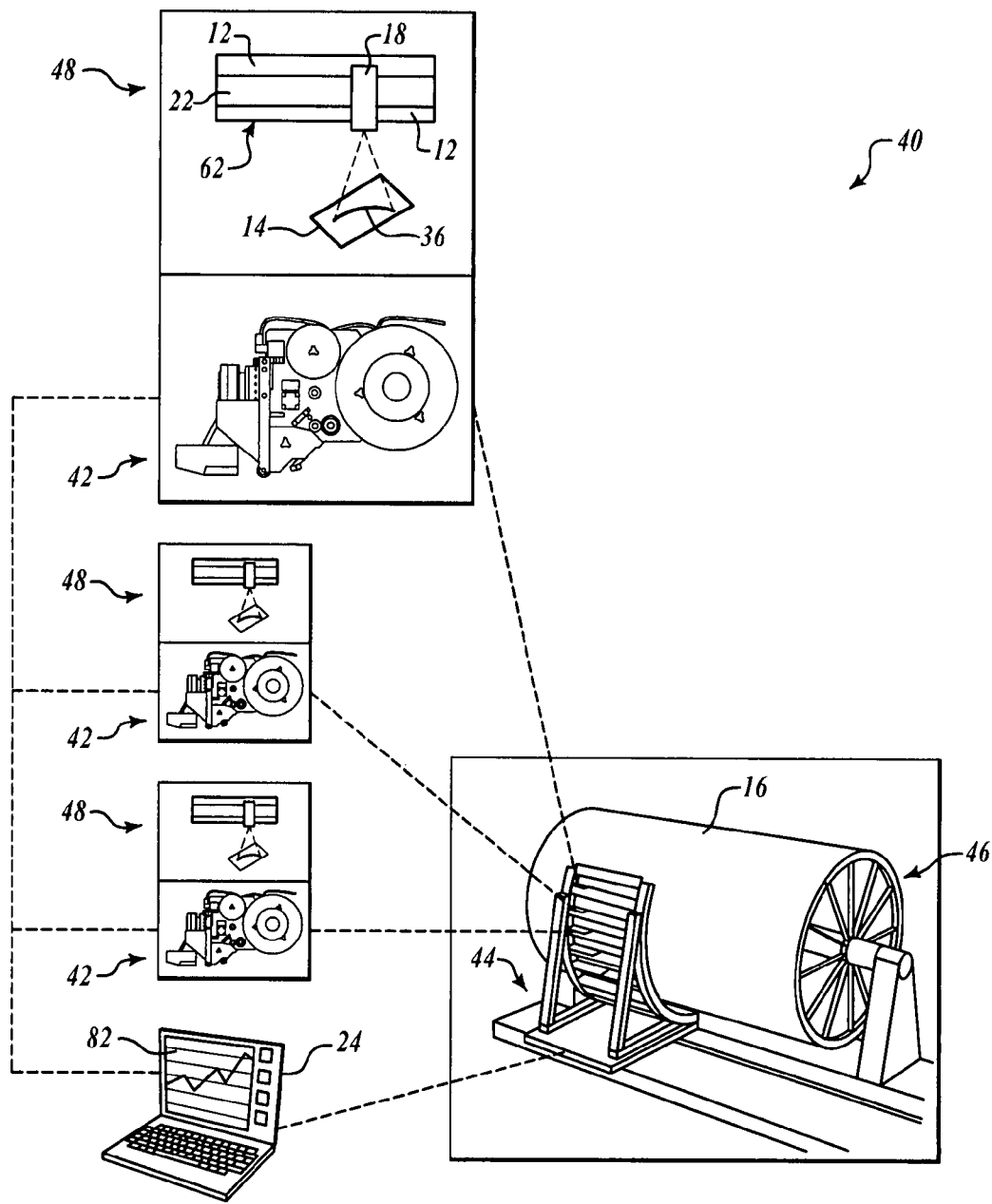
FIG. 2 is an isometric view of an exemplary system for manufacturing composite components according to another embodiment.

To that end and referring now to FIG. 2, an exemplary system 40 can manufacture composite components in accordance with an embodiment. In this embodiment, the system 40 includes a plurality of head assemblies 42 coupled to a translation platform 44 and operatively positioned proximate a forming tool (or mandrel) 46. The translation platform 44 is configured to systematically move the head assemblies 42 along translation paths (for example, three-dimensional paths) proximate the forming tool 46, and each head assembly 42 is configured to perform placement and consolidation of a fiber-reinforced composite tape material onto the forming tool 46 to produce a laminated composite workpiece 16, as described more fully below. Each head assembly 42 is operatively coupled to a monitoring unit 48 configured to perform in-process inspections of the manufacturing processes (in this non-limiting example, composite tape application processes) performed by the head assembly 42. Structural and operational features of the monitoring unit 48 are described more fully below. Information regarding exemplary components of the system 40, including the head assembly 42 and the monitoring unit 48, is discussed in U.S. patent application Ser. No. 11/383,681, filed May 16, 2006 and published as U.S. Patent Publication No. 2007/0277919, the contents of which are hereby incorporated by reference.

A data processing system 24 is operatively coupled to the translation platform 44 and to the head assemblies 42. In addition to the functions described above and that will be described further below, the data processing system 24 is configured to implement a control code that transmits control signals to the translation platform 44 and the head assemblies 42. The control signals command the movement and functions of the translation platform 44 and the head assemblies 42, thereby causing automated (or semi-automated) manufacturing of the laminated composite workpiece 16 on the forming tool 46. In the exemplary embodiment shown, the manufacturing system 40 is a multi-head tape lamination machine (MHTLM). In one particular embodiment, the system 40 includes eight head assemblies 42 for the placement of composite tape. However, in other embodiments, any desired number of head assemblies 42 may be employed.

Figure 3:
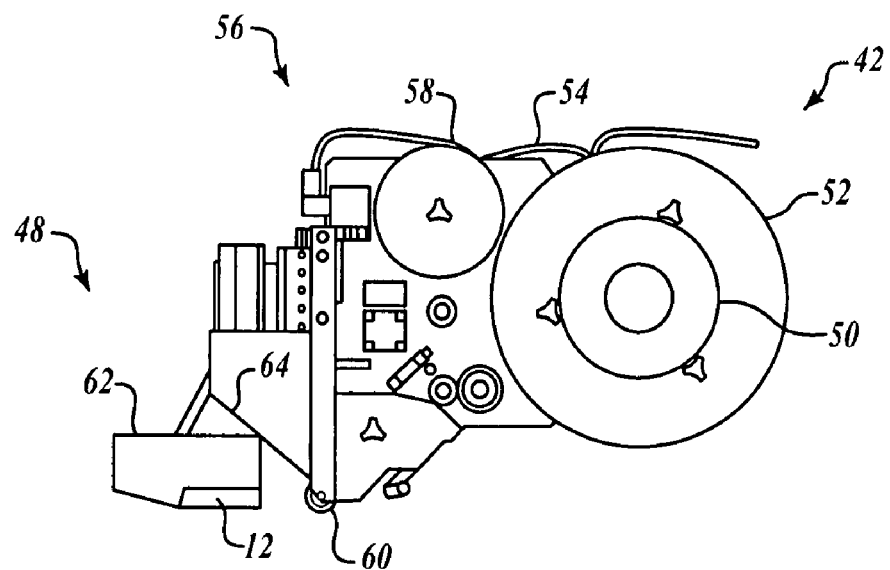
FIG. 3 is an enlarged side view of an exemplary head assembly of the system of FIG. 2 according to another embodiment.

Referring now to FIG. 3, the head assembly 42 includes a spindle 50 configured to retain a roll 52 of a fiber-reinforced composite tape 54, and a feed assembly 56 configured to receive, guide, feed, and apply the tape 54 from the roll 52 onto the workpiece 16. More specifically, the feed assembly 56 includes a feed roller 58 that receives the tape 54 from the roll 52, and a compaction roller 60 that applies and compresses the tape 54 onto the workpiece 16. The feed assembly 56 may include a variety of other components (for example, motors, rollers, guides, sensors, and the like) configured to cooperatively receive, feed, and guide the tape 54 from the roll 52 to the compaction roller 60, as described more fully, for example, in U.S. Pat. No. 6,799,619 B2 issued to Holmes et al., and U.S. Pat. No. 6,871,684 B2 issued to Engelbart et al., as well as in co-pending, commonly-owned U.S. patent application Ser. Nos. 09/998,478 (published as U.S. Patent Publication No. 2003/0102070), which patents and pending patent applications are incorporated herein by reference.

Figure 4:
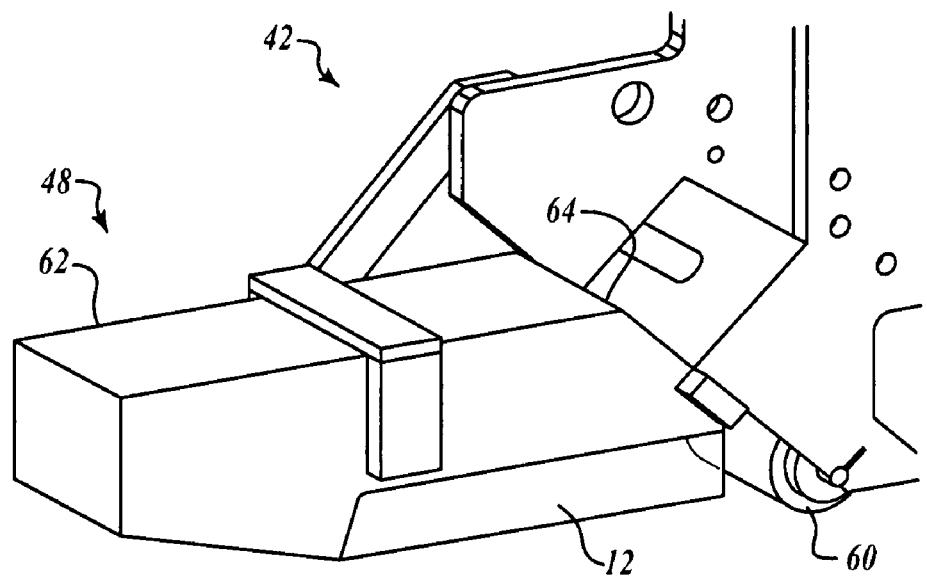
FIG. 4 is an enlarged isometric view of an exemplary monitoring unit of the head assembly of FIG. 3.
Figure 5:
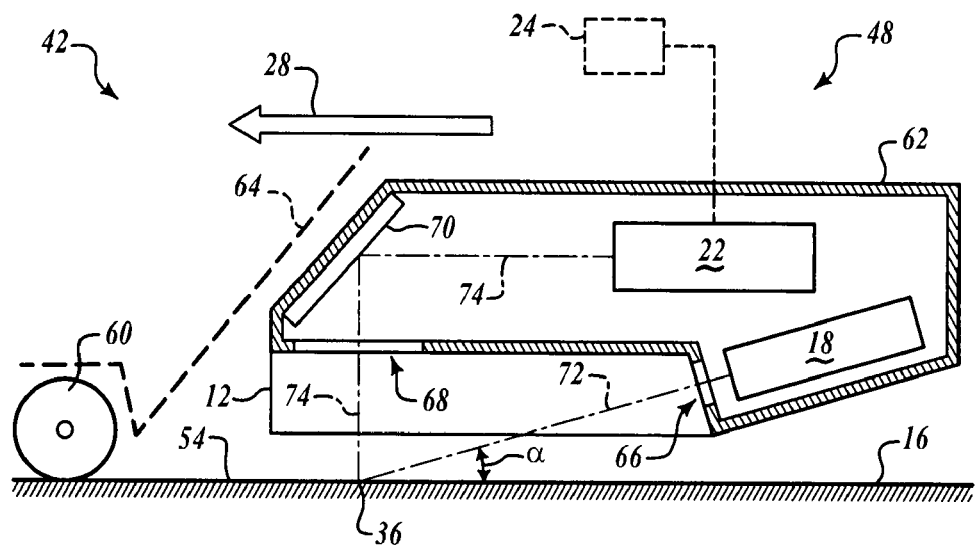
FIG. 5 is a side cross-sectional view of the monitoring unit of FIG. 4.

Referring now to FIGS. 4-5, the monitoring unit 48 includes all of the components of the system 10 (FIG. 1) except for the data processing system 24. However, in some embodiments the monitoring unit 48 can also include a data processing system 24 that is sized to fit within the monitoring unit 48. Two of the light sources 12 are disposed on opposite sides of a bottom portion of a housing 62. The housing 62 is coupled to a structural portion 64 of the head assembly 42 proximate to the compaction roller 60, and includes apertures 66 and 68. A mirror 70 is positioned within the housing 62 proximate the aperture 68. In one particular embodiment, the light source 18 includes two laser fan-beam projectors such as Lasiris Model MFL units commercially-available from Stocker Yale of Salem, N.H., USA, and the sensor 22 is a camera such as a Model KP-M22A video camera, commercially-available from Hitachi Kokusai Electric Incorporated of Tokyo, Japan. In other embodiments, any suitable laser scanners or cameras may be used.

As the head assembly 42 is traversed over the workpiece 16 in a direction of travel indicated by the arrow 28, the light source 18 provides fan beams 72 that are projected through the aperture 66 onto the composite tape 54 as the signature line 36 after the composite tape 54 has been applied to the workpiece 16 by the compaction roller 60. The fan beams 72 intersect the composite tape 54 at an incidence angle $\alpha$ and produce the signature line 36 that extends laterally (or transversely) across the composite tape 54. In one particular embodiment, the incidence angle $\alpha$ is approximately 15 degrees. However, in other embodiments, incidence angles between approximately 10 degrees and approximately 35 degrees may be used. Alternately, any other suitable incidence angle may be used. As described more fully below, the monitoring unit 48 is configured to detect and characterize various features of interest (for example edges, gaps, wrinkles, puckers, overlaps, foreign object debris (FOD), and the like) along the signature line 36. Preferably, the monitoring unit 48 is positioned such that the signature line 36 is relatively close (that is, as close as practical) to the compaction roller 60 so that features of interest may be detected relatively quickly in the manufacturing process.

A reflected beam 74 reflects upwardly from the composite tape 54, passes into the housing 62 through the aperture 68, and reflects from the mirror 70 to the sensor 22. In one particular embodiment, the reflected beam 74 reflects approximately normally from the composite tape 54. However, in other embodiments, any other suitable reflection angle may be used. The sensor 22 receives the reflected beam 74 and transmits data to the data processing system 24 for analysis and display.

Figure 6:
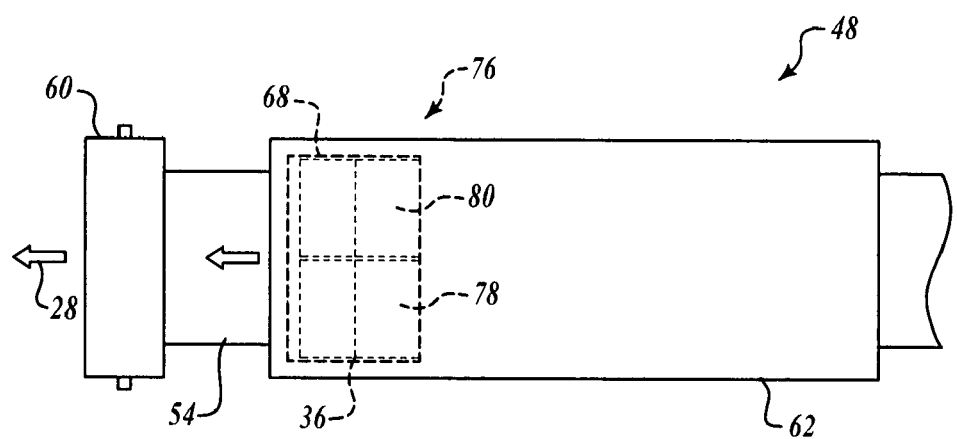
FIG. 6 is a top view of the monitoring unit of FIG. 4.

Referring now to FIG. 6, in one exemplary embodiment a field of view 76 of the sensor 22 through the aperture 68 may be divided into regions of interest (ROI) 78 and 80, and the illuminated signature line 36 is approximately centered within each ROI field of view 76.

Now that an exemplary embodiment for monitoring automated composite fabrication processes has been explained, exemplary embodiments for identifying features in a workpiece will be explained.

Exemplary Embodiments for Identifying Features in a Workpiece

Referring now to FIGS. 1-6, the data processing system 24 may be configured to analyze the data provided by the sensor 22 to determine whether any features of interest are present, and if so, may characterize such features of interest into various categories including, for example, edges, gaps, wrinkles, overlaps, and various types of FOD. The data processing system 24 may be further configured to perform various functions based on the results of the detection and characterization of a feature of interest, including displaying the data from the sensor 22 via a display 82 (FIG. 2), identifying the feature of interest, notifying an operator, recording information regarding the feature of interest (such as location, type, or the like), and if desired, halting manufacturing operations to permit further inspection and remedial action.

Generally, any of the methods described herein can be implemented using software, firmware (for example, fixed logic circuitry), hardware, manual processing, or any combination of these implementations. The terms "module," "functionality," and "logic" generally represent software, firmware, hardware, or any combination thereof. In the case of a software implementation, the module, functionality, or logic represents program code that performs specified tasks when executed on processor(s) (for example, any of microprocessors, controllers, and the like). The program code can be stored in one or more computer readable memory devices. Further, the methods and systems described herein are platform-independent such that the techniques may be implemented on a variety of commercial computing platforms having a variety of processors.

Furthermore, one or more of the methods disclosed herein may be described in the general context of computer executable instructions. Generally, computer executable instructions can include routines, programs, objects, components, data structures, procedures, modules, functions, and the like that perform particular functions or implement particular abstract data types. The methods may also be practiced in a distributed computing environment where functions are performed by remote processing devices that are linked through a communications network. In a distributed computing environment, computer executable instructions may be located in both local and remote computer storage media, including memory storage devices. For example, in alternate embodiments, one or more of the above-noted operations of the data processing system 24 may be distributed to one or more separate processing units, such as processing units installed within each head assembly 42, or within each monitoring unit 48, or any other suitable arrangement.

Figure 7:
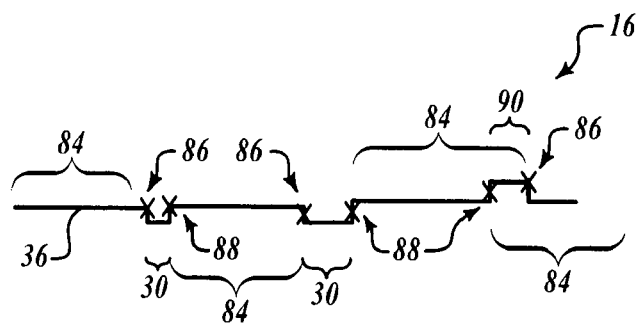
FIG. 7 illustrates steps in an exemplary laser line.

Referring now to FIGS. 1 and 7, information contained within the signature line 36 will be discussed. The signature line 36 is used to produce single-pixel addresses of best-guess edge locations in the two-dimensional image, which in some embodiments may then be used to seed a constrained edge-following algorithm that calculates the best fit of the nearest line. The relative difference between the light and dark areas may be quite small, and thus edge-finding algorithms discussed further below integrate information from as much of the image as possible in order to produce the best measure of location.

Thus, a starting point in refining attributes of features of a workpiece, such as locations of edges of a gap or overlap, is to determine best-guess edge locations in the two-dimensional image as highlighted by steps in the three-dimensional laser signature line 36 that crosses the two-dimensional image. These locations are relatively easy to detect by any number of means, and are caused simply by the change in height of the surface of the workpiece 16. It will be appreciated that the direction, or polarity, of the step is determined by the sign of the change in height. Therefore, the nature of a joint (that is, two consecutive edges) is determined to be either a gap or an overlap of material simply by the order of the succession of polarity—that is, minus-to-plus or plus-to-minus.

With this context in mind and referring to FIG. 7, the three-dimensional laser signature line 36 across tows 84 of the workpiece 16 includes easily-detected steps 86 and 88 along it due to changes in thickness of the material of the workpiece 16. The steps 86 go in one direction on one side of a gap 30 and may be assigned a "negative" polarity. The steps 88 go in the other direction on the opposing side of the gap 30 from the steps 86 and may be assigned a "positive" polarity. It will be noted that the horizontal ordering of negative and positive polarities of the steps 86 and 88 for the gaps 30 are reversed from the horizontal ordering of the steps 88 and 86 for an overlap 90.

Figure 8:
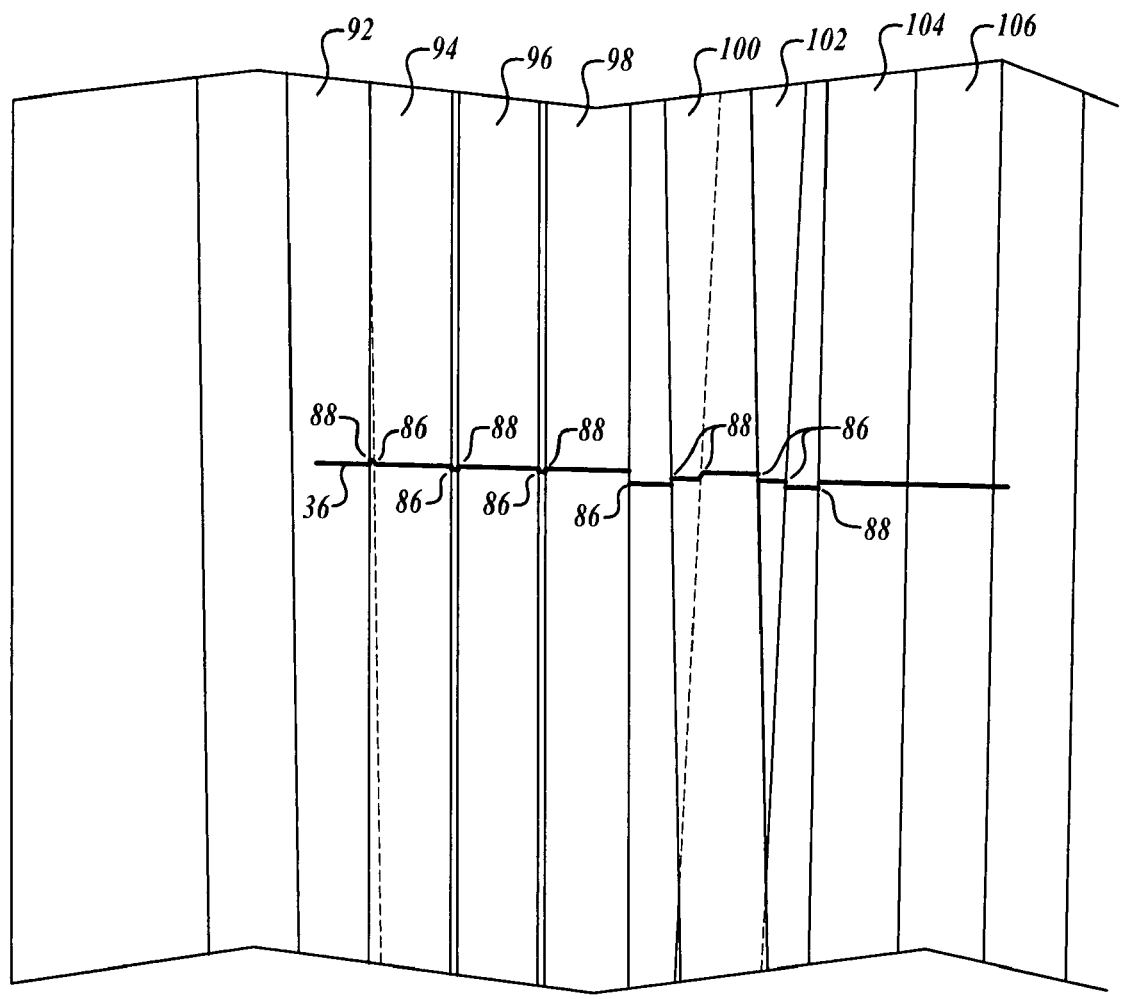
FIG. 8 illustrates an exemplary laser signature line illuminating composite tows.

Referring now to FIG. 8, the three-dimensional laser signature line 36 spans several gaps and overlaps between composite tows. The following description proceeds from left-to-right as shown in FIG. 8. A tow 92 slightly overlaps a tow 94, thereby resulting in a "positive" polarity step 88 and a "negative" polarity step 86. A small gap exists between the tow 94 and a tow 96, thereby resulting in a "negative" polarity step 86 and a "positive" polarity step 88. A medium gap exists between the tow 96 and a tow 98, thereby also resulting in a "negative" polarity step 86 and a "positive" polarity step 88.

Still referring to FIG. 8, a tow 100 is skewed downwardly toward the right and a tow 102 is skewed downwardly toward the left. A large gap exists between the tow 98 and the tow 100, thereby also resulting in a "negative" polarity step 86 and a "positive" polarity step 88. The tows 100 and 102 then overlap each other, thereby resulting in a "positive" polarity step 88 and a "negative" polarity step 86. A gap exists between the tow 102 and a tow 104, thereby resulting in a "negative" polarity step 86 and a "positive" polarity step 88. The tow 104 exactly butts against a tow 106, and no resultant steps 86 or 88 appear in the signature line 36.

Figure 9A:
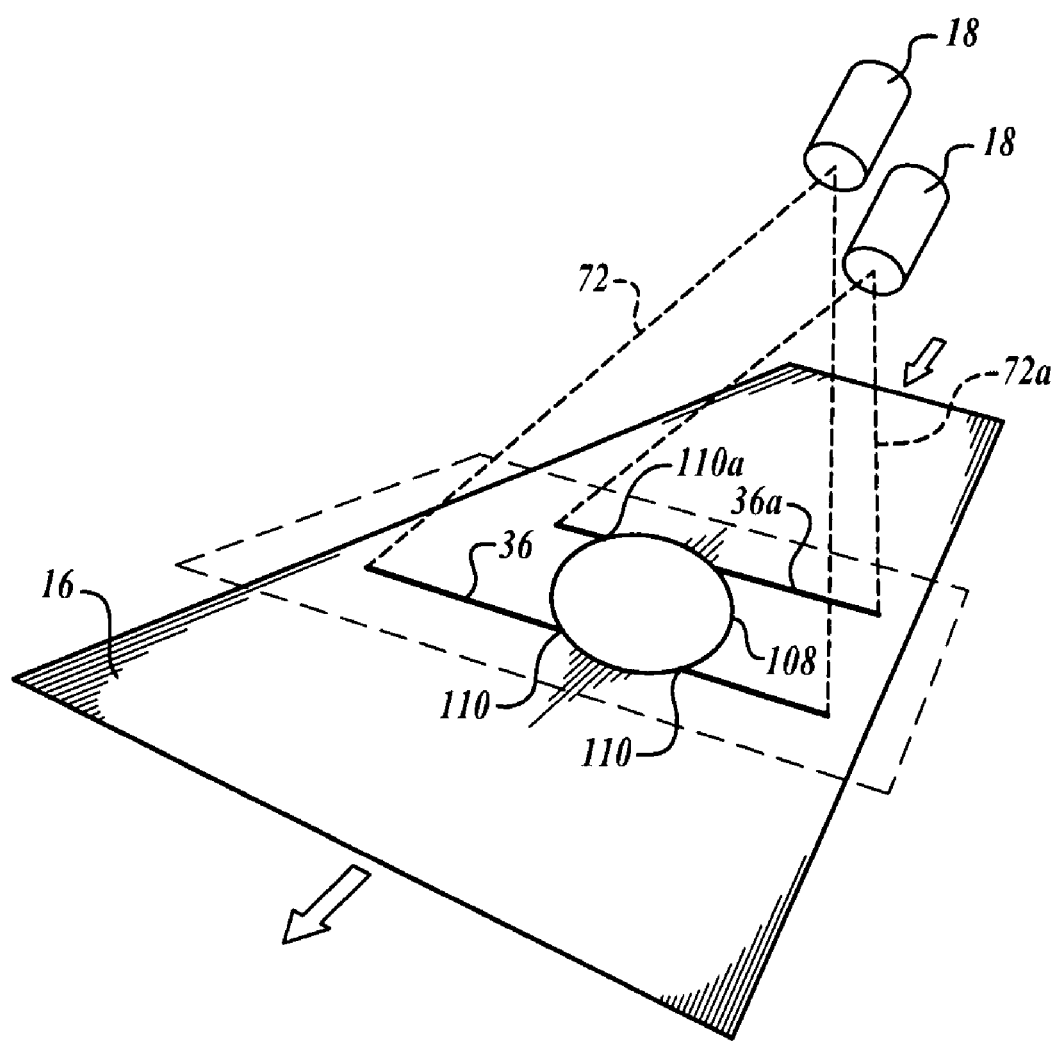
FIG. 9A illustrates exemplary illumination of an image frame by more than one laser.
Figure 9B:
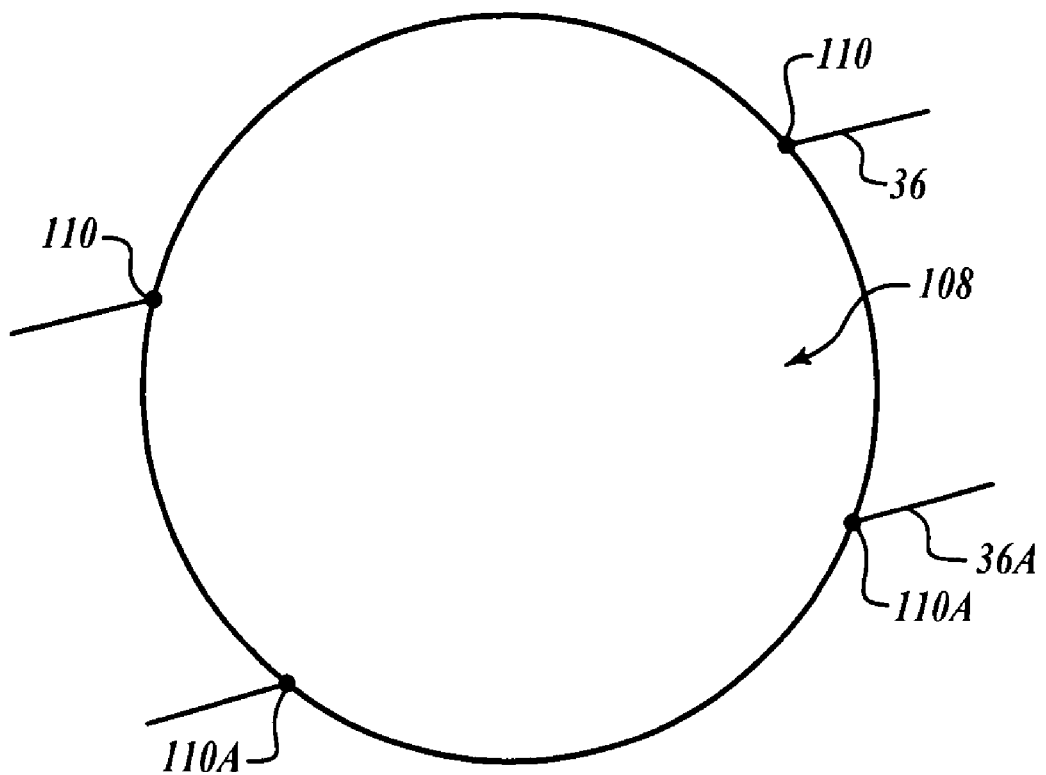
FIG. 9B illustrates a feature identified in FIG. 9A.

Referring now to FIGS. 9A and 9B, in some embodiments more than one signature line 36 is generated in order to identify a feature such as a circular hole in a workpiece. For example, the workpiece 16 can have a flaw or an intentionally-inserted feature in the shape of a circular hole 108. When the signature line 36 coincides with the diameter of the circular hole 108, attributes of the hole 108 such as the location of the circumference of the hole 108 can be determined with only the one signature line 36. In the event that the signature line 36 does not coincide with the diameter of the hole 108, then more than one signature line is used to identify attributes of the hole 108.

For example, a light source 18 generates a fan beam 72 that traces a signature line 36 across the hole 108 in the workpiece 16. The signature line 36 does not coincide with the diameter of the hole 108 (as would more likely than not be the case). The signature line 36 stops at points 110 on the circumference of the hole 108. An edge following algorithm, such as that discussed further below, can be used to detect a circular edge from the points 110 used as "seeds", as discussed below. However, it may be desirable to provide more points to increase accuracy and robustness. To that end, another light source 18 generates another fan beam 72A that traces another signature line 36A across the hole 108. The signature line 36A stops at points 110A on the circumference of the hole 108. Pattern recognition algorithms known by those of ordinary skill in the art can be used to fit the points 110 and 110A to the circumference of the hole, thereby identifying the location of the hole 108. It will be appreciated by those of ordinary skill in the art that the circle can be identified with three points. It will also be appreciated by those of ordinary skill in the art that use of four points (as shown) to identify the circle provides redundancy and, therefore, robustness to the process.

Figure 10A:
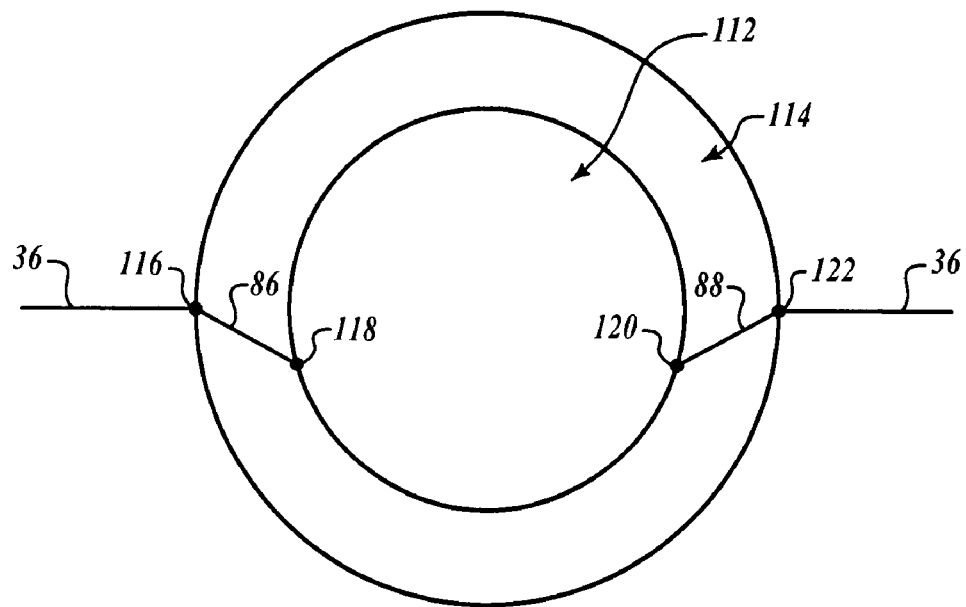
FIG. 10A is a top view of an exemplary laser signature line illuminating a chamfered hole.
Figure 10B:
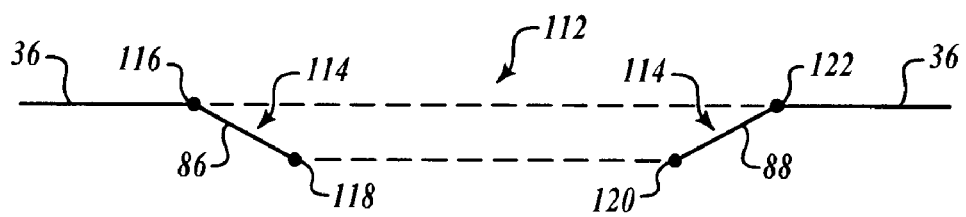
FIG. 10B is a side view of the laser signature line of FIG. 10A illuminating the chamfered hole of FIG. 10A.

Referring now to FIGS. 10A and 10B, only one signature line 36 can be used to identify a chamfered hole 112. The chamfered hole has a chamfer 114. To identify the chamfer 114, the signature line 36 need not coincide with the diameter of the hole 112. The signature line 36 has a "negative" polarity step 86 between a point 116 on the circumference of the hole 112 and a point 118 at the end of the chamfer 114. Likewise, the signature line 36 has a "positive" polarity step 88 between a point 120 at the end of the chamfer 114 and a point 122 on the circumference of the hole 112. The "negative" polarity step 86 between the points 116 and 118 and the "positive" polarity step 88 between the points 120 and 122 can be used to identify the chamfer 114 in the same manner described below for identifying edge locations. As discussed above, use of more than one signature line can increase the number of points that can be used as "seeds", thereby providing redundancy and, therefore, robustness to the process.

Figure 11:
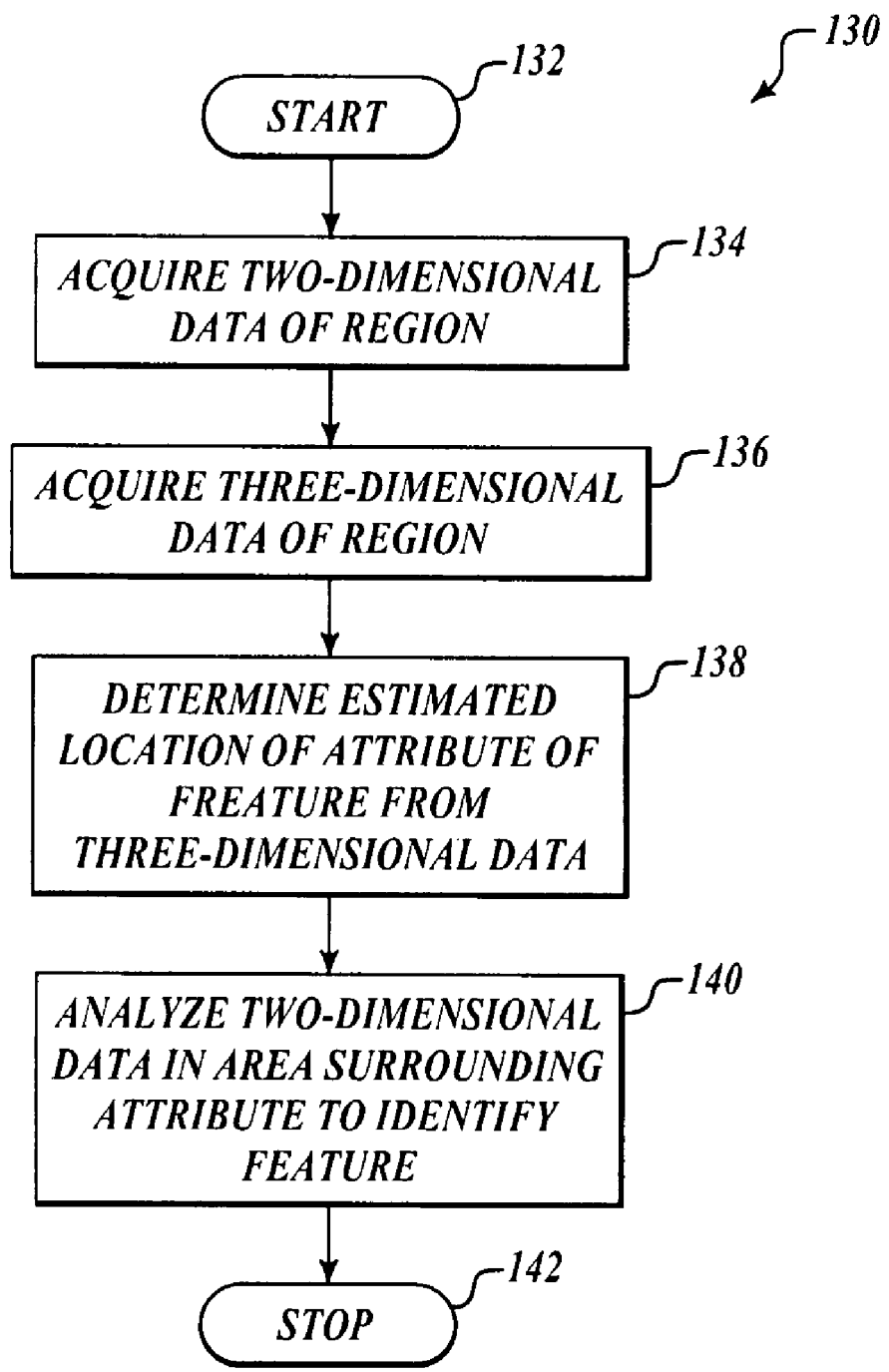
FIG. 11 is a flow chart of an exemplary method of identifying a feature of a workpiece according to an embodiment.

Referring now to FIG. 11 and FIG. 1, in general an exemplary method 130 can be executed to identify a feature of a workpiece. The method 130 begins at a block 132. At a block 134, two-dimensional data of a region of a workpiece is acquired. For example, the region 14 can be illuminated by the light sources 12 and a two-dimensional image acquired by the sensor 22 can be provided to the data processing system 24.

At a block 136 three-dimensional data of a portion of the workpiece is acquired. For example, the light source 18 can generate the signature line 36 across the workpiece 16 and three-dimensional information acquired by the sensor 22 can be provided to the data processing system 24. No temporal or sequential implication is intended by use of separate process blocks 134 and 136. In exemplary embodiments, the light sources 12 and 18 illuminate their respective features simultaneously and the sensor 22 senses the image as one frame of information. Thus, the process blocks 134 and 136 can be considered to occur simultaneously.

At a block 138 an estimated location of an attribute of a feature of the workpiece is determined from the three-dimensional data. For example, a "best-guess" estimate of an edge location in the two-dimensional image can be obtained by using location of the appropriate step 86 or 88 in the three-dimensional laser signature line 36 that crosses the two-dimensional image.

At a block 140 the feature is identified by analyzing the two-dimensional data in an area surrounding the estimated location of the attribute. For example, a search area can be centered around the estimated location of the attribute—such as location of the step 86 or 88 (FIGS. 7 and 8) as an estimate for location of an edge of a line. If desired, the two-dimensional data can be analyzed iteratively as described below, increasing the height of the search window and reducing the width of the search window with each iteration. When the analysis of the block 140 is completed, the method 130 stops at a block 142.

Figure 12:
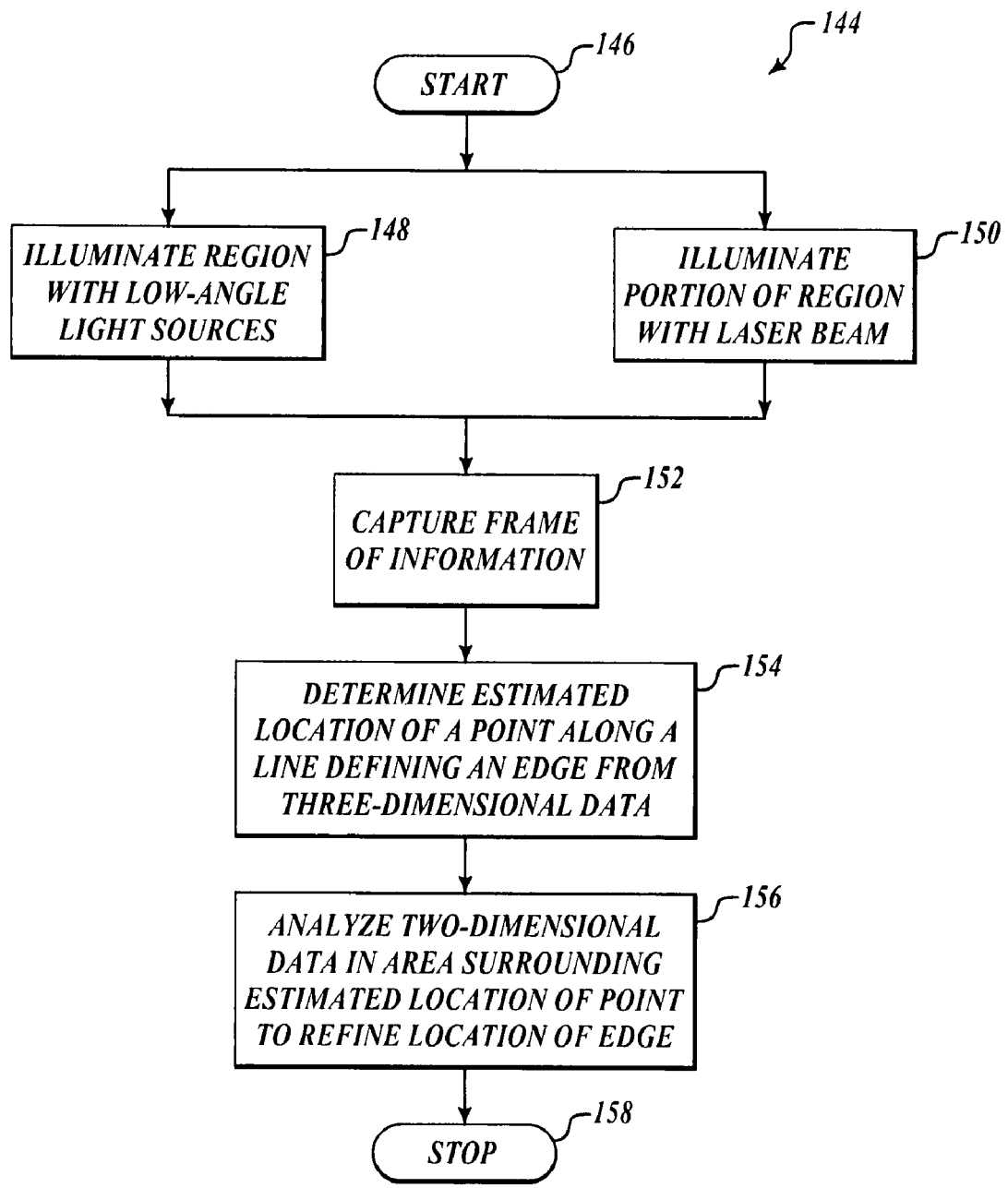
FIG. 12 is a flow chart of an exemplary method of refining location of an edge according to an embodiment.

Referring now to FIG. 12 and FIG. 1, in an exemplary embodiment a method 144 can be executed to refine location of an edge of a line. The method 144 starts at a block 146. At a block 148, at least a region of a workpiece is illuminated with a pair of light sources that are disposed at a low angle of incidence. For example, the region 14 can be illuminated by the light sources 12.

At a block 150 a portion of the region of the workpiece is illuminated with a light source that is disposed at an angle of incidence relative to a plane of the region that is greater than the low angle of incidence. For example, the light source 18 can generate the signature line 36 across the workpiece 16. Again, it will be understood that no temporal or sequential implication is intended by use of separate process blocks 148 and 150. In exemplary embodiments, the light sources 12 and 18 illuminate their respective features simultaneously. Thus, the process blocks 148 and 150 can be considered to occur simultaneously.

At a block 152 a frame of information is captured. For example, an image can be acquired by the sensor 22 and provided to the data processing system 24. The frame of information includes two-dimensional information of the image, as illuminated by the light sources 12, and three-dimensional information of the image, as illuminated by the light source 18. Once again, no temporal or sequential separation from processing at the blocks 148 and 150 is intended by use of a separate process block 152. In exemplary embodiments, the light sources 12 and 18 illuminate their respective features simultaneously and the sensor 22 contemporaneously acquires the frame of information and provides the frame of information to the data processing system 24. Thus, the process blocks 148, 150, and 152 can be considered to occur simultaneously.

At a block 154 an estimated location of a point along a line defining an edge within the workpiece is determined from three-dimensional data from the frame of information. For example, the pixel location of a step 86 or 88 (FIGS. 7 and 8) is used as a "best-guess" estimate of an edge of a line, such as an edge of a line of composite tape or tow.

At a block 156, location of the edge is refined by analyzing two-dimensional data from the frame of information in an area surrounding the estimated location of the point. For example, the pixel location of the step 86 or 88 (FIGS. 7 and 8) is used as a "seed" for a search window. A search window is centered around the pixel location of the step 86 or 88 (FIGS. 7 and 8). The two-dimensional data can be analyzed iteratively as described below, increasing the height of the search window and reducing the width of the search window with each iteration. When the analysis of the block 156 is completed, the method 144 stops at a block 158.

Figure 13:
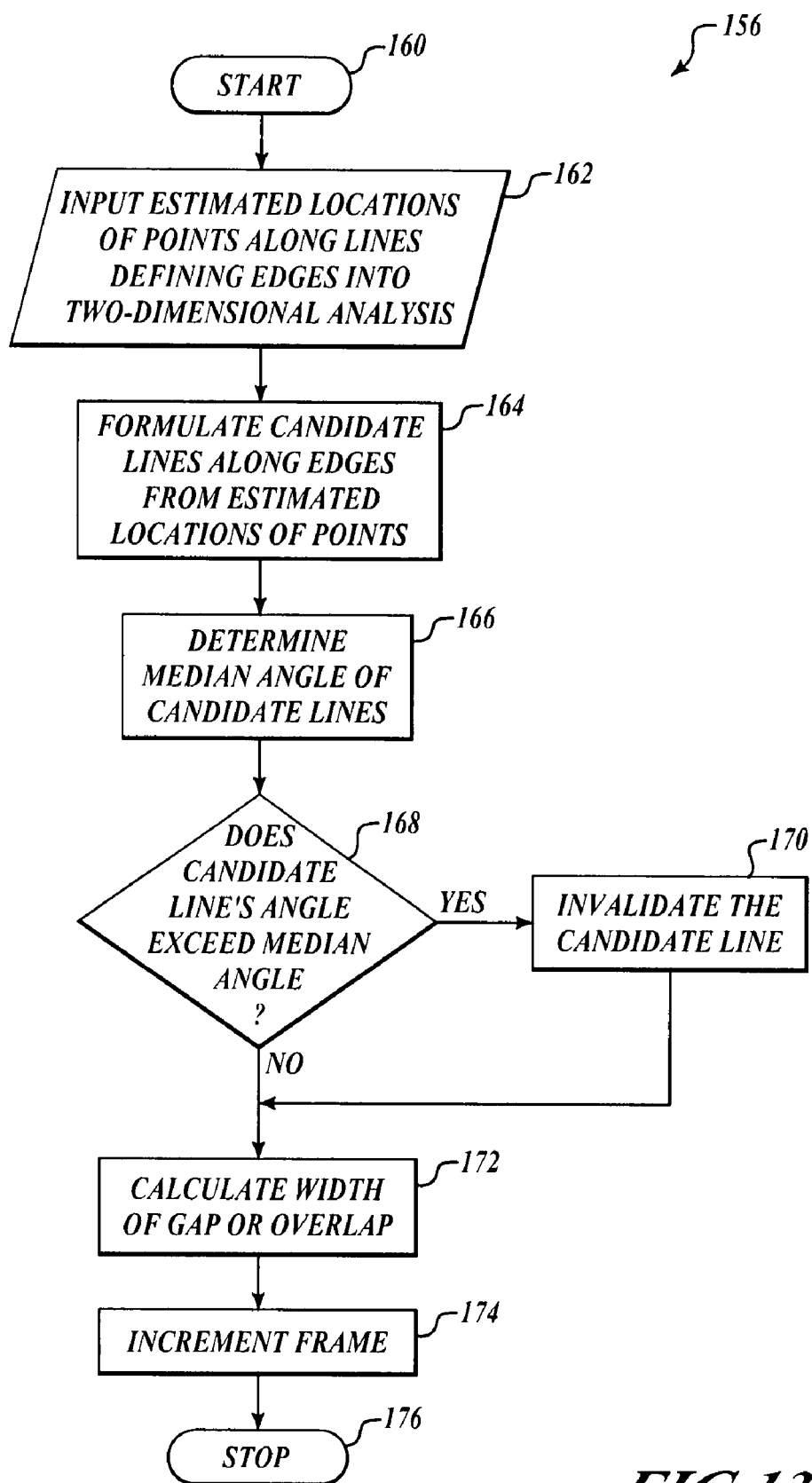
FIG. 13 is a flow chart of details of a portion of the flow chart of FIG. 12.

Referring now to FIG. 13, details of exemplary processing of the block 156 (FIG. 12) will now be explained. The processing of the block 156 starts at a block 160. At an input block 162, the estimated locations of points along lines that define edges are input into analysis algorithms of two-dimensional information. For example, for each image frame acquired by the sensor 22, all of the steps 86 and 88 (FIGS. 7 and 8) along the signature line 36 are detected. The row and column pixel address and the associated polarity (that is, "positive" or "negative", as discussed above) of each step are compiled into a list of "seed" or estimated locations. The list of seed locations is used as a list of estimated locations or starting points to "cue" a two-dimensional edge finding algorithm (described below).

At a block 164, candidate lines are formulated along edges from the estimated locations of the points input at the block 162. A two-dimensional edge finding algorithm (described below) generates a best-fitting edge line from each of the listed estimated, "seed" locations determined from the steps 86 and 88 (FIGS. 7 and 8) in the signature line 36. As will be explained below, the best-fitting edge lines are generated according to nearness and polarity of the two-dimensional appearance.

At a block 166, an angle of each candidate line generated at the block 166 for the frame of information is determined and a median angle is determined from all of the angles of the candidate lines. At a decision block 168, a determination is made whether a candidate line's angle exceeds the median angle. For example, when the workpiece 16 is made of composite tape or tows, the candidate lines should all be substantially parallel to each other, within a range of degrees. The range of degrees can depend on the nature of the workpiece under measurement. For example, for composite tape or tow, the range of degrees can be around two degrees. If a candidate line's angle exceeds the median angle, then at a block 170 the candidate line is invalidated and is removed from further processing and processing of the block proceeds to a block 172. If a candidate's line does not exceed the median angle, then processing of the block 156 also proceeds to the block 172.

At the block 172 width of a most-probable gap or overlap between components of the workpiece 16, such as composite tape or tows. For example, geometric distance between adjacent candidate lines of a pair of candidate lines can be determined at an average image row location of the two associated seed pixels for the candidate lines.

After gap or overlap measurements are made, at a block 174 the image frame is incremented. The processing of the block 156 for the image frame stops at a block 176. Processing of the block 156 can be performed again for the next image frame, as desired.

Figure 14:
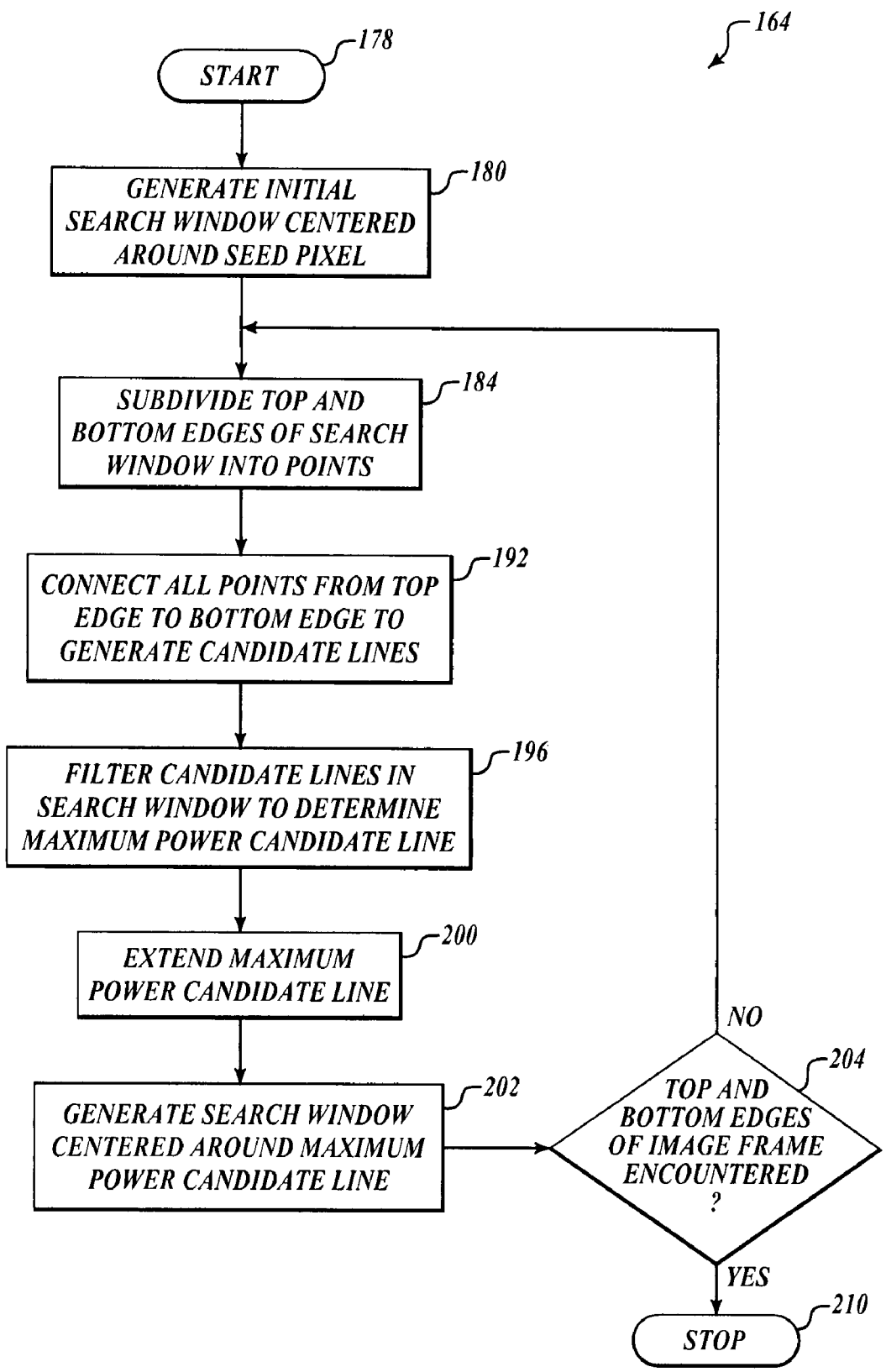
FIG. 14 is a flow chart of details of a portion of the flow chart of FIG. 13.

Referring now to FIG. 14, at the block 164 an exemplary two-dimensional edge finding algorithm formulates searches for an equation of a best edge-like path through a contrast image starting from the estimated location of an edge, that is the "seed" pixel, and continues refinement through a series of iterations. Processing of the block 164 starts at a block 178.

Figure 15C:
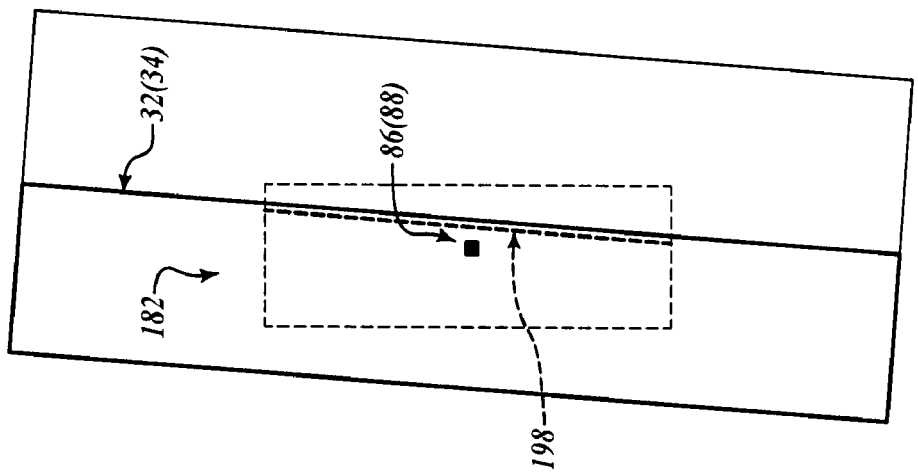
FIGS. 15A-15C illustrate stages of a first iteration of search window processing by an exemplary edge finding algorithm.
Figure 15B:
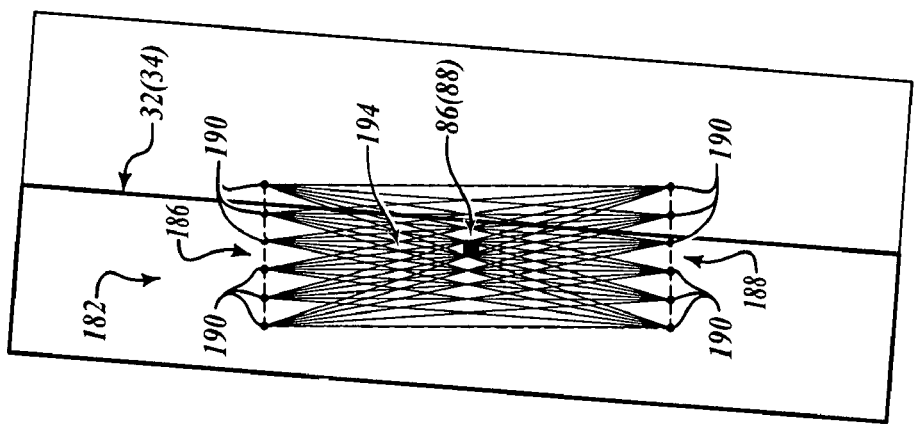
Figure 15A:
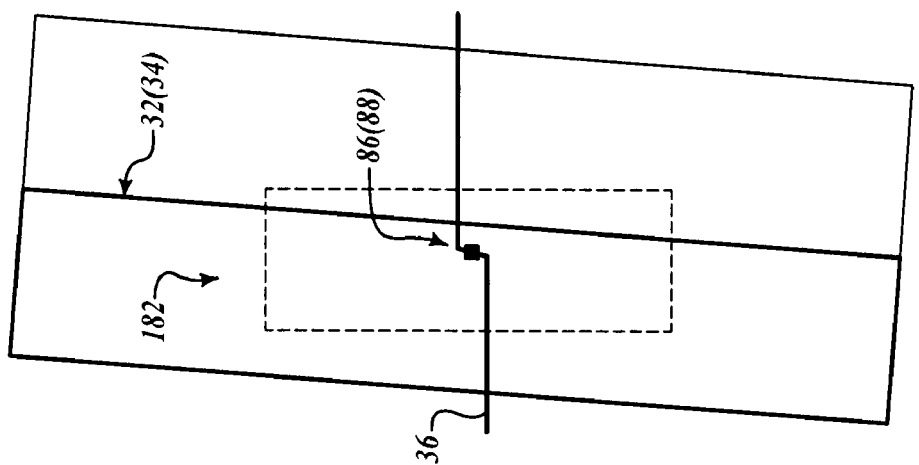

Referring now to FIGS. 14 and 15A, at a block 180 an initial search window 182 is centered around the location of the seed pixel—that is, the pixel location of the step 86 or 88 along the signature line 36 (that is, the three-dimensional information) that is seen near the edge 32 or 34 (that is the two-dimensional information). The initial search window 182 suitably is a rectangle. The initial search window 182 has a width sufficient to cover potential misplacement of the seed pixel relative to the real edge, and a height short enough to help ensure that angular variation of the tape or tow relative to the sensor 22 (FIG. 1) will be contained within the top and bottom edges.

At a block 184, top and bottom edges 186 and 188 of the search window 182 are subdivided into points 190.

At a block 192 all of the points 190 along the top edge 186 are connected to all of the points 190 along the bottom edge 188. Connecting all of the points 190 in this manner generates candidate edge filter kernel lines 194.

At a block 196 all of the candidate edge filter kernel lines 194 are filtered. Exemplary filtering is discussed in detail further below. Filtering the candidate edge filter kernel lines 194 at the block 196 determines which of the candidate edge filter kernel lines 194 has a maximum power level. Referring additionally to FIG. 15C, a line 198 is identified as having the maximum filter output power and is retained for further processing in a next iteration.

Figure 16C:
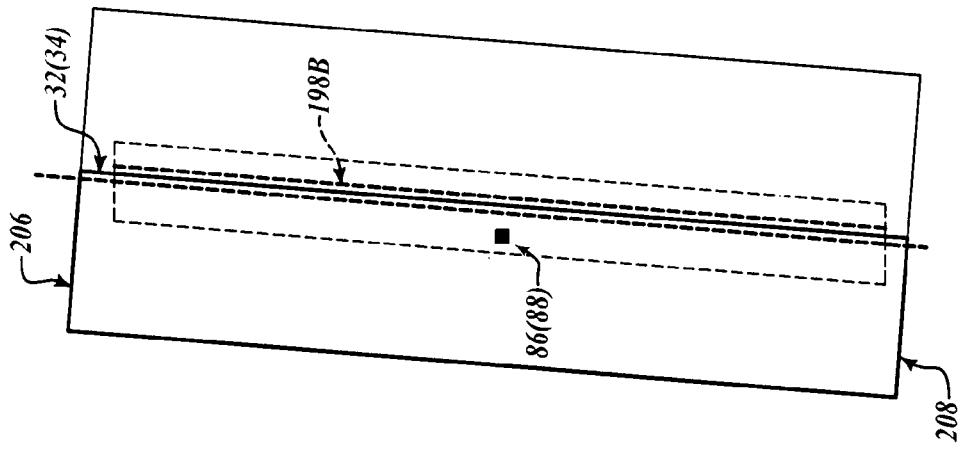
FIGS. 16A-16C illustrate stages of a second iteration of search window processing by an exemplary edge finding algorithm.
Figure 16B:
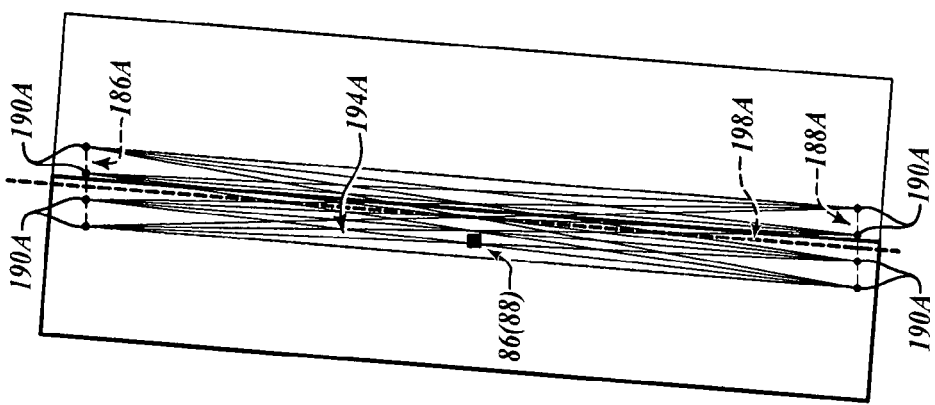
Figure 16A:
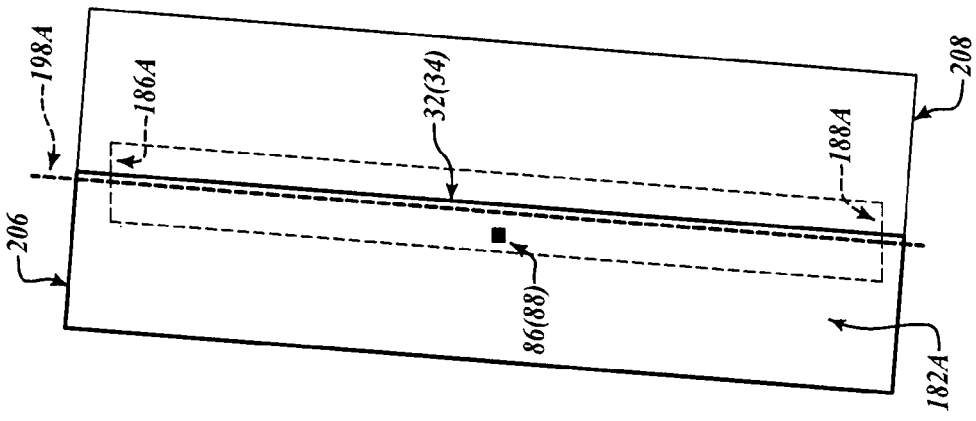

Referring now to FIGS. 14 and 16A, at a block 200 the line 198 (FIG. 15C) having the maximum filter output power from the previous iteration is extended vertically by a predetermined distance and is now represented as a line 198A.

At a block 202 a new search window 182A is generated and is centered around the line 198A. The search window 182A suitably can be any quadrilateral as desired. Length of the search window 182A is extended beyond that of the search window 182 (FIGS. 15A-15C) and width of the search window 182 is reduced from that of the search window 182 (FIGS. 15A-15C).

At a decision block 204, a determination is made whether or not a top edge 206 and a bottom edge 208 of the image frame have been encountered by a top edge 186A and a bottom edge 188A, respectively, of the search window 182A. If so, then processing of the block 164 stops at a block 210.

If the top edge 206 and the bottom edge 208 have not been encountered by the top edge 186A and the bottom edge 188A, respectively, then processing of the block 164 returns to the block 184 for a next iteration. Referring now to FIG. 14 and FIG. 16B, at the block 184, the top and bottom edges 186A and 188A are subdivided into points 190A. At the block 192 all of the points 190A along the top edge 186A are connected to all of the points 190A along the bottom edge 188A, thereby generating candidate edge filter kernel lines 194A. At the block 196 all of the candidate edge filter kernel lines 194A are filtered. Referring additionally to FIG. 16C, a line 198B is identified as having the maximum filter output power and is retained for further processing in a next iteration. At the block 200 the line 198B is extended vertically by a predetermined distance. At the block 202 a new search window 182A is generated as discussed above and is centered around the line 198B. At the decision block 204, a determination is made whether or not the top edge 206 and the bottom edge 208 of the image frame have been encountered, as discussed above.

Figure 17:
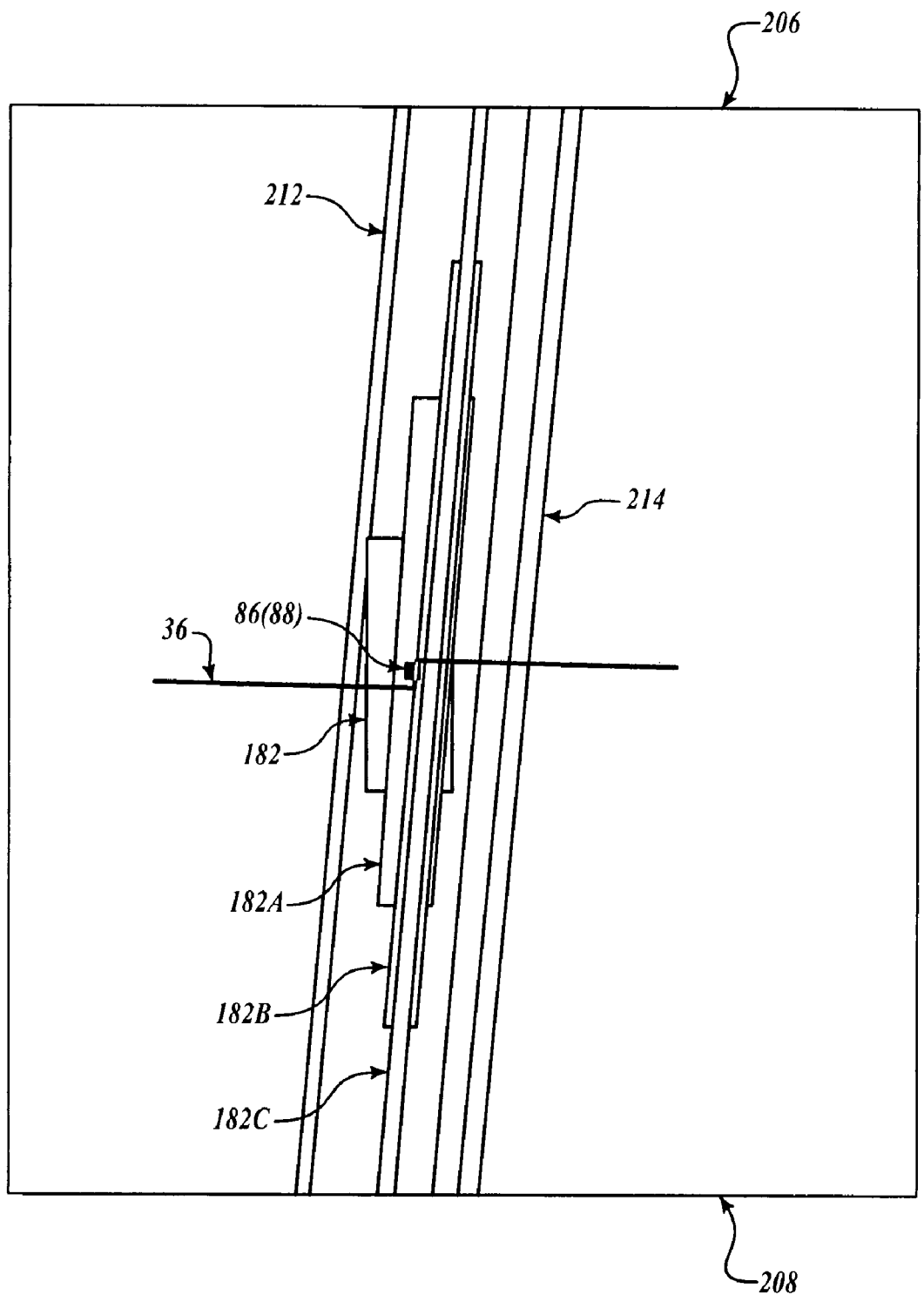
FIG. 17 superimposes stages of several iterations of search window processing by an exemplary edge finding algorithm.

Referring now to FIGS. 14 and 17, progression of processing of the block 164 is seen through several iterations. The step 86 or 88 is detected in the laser signature line 36. In this illustration, spurious bright lines 212 and 214 that are not associated with changes in surface height of the workpiece (that is, a gap or an overlap) do not appear along the signature line 36 as either a step 86 or a step 88. Thus, the locations of the spurious lines 212 and 214 are ignored and are not input into processing as estimated pixel seed locations. A first iteration searches the initial search window 182 in the image frame, as discussed above. Additional searching follows in subsequent iterations in the search window 182A, in a subsequent search window 182B, and in a further subsequent search window 182C until the top and bottom edges 206 and 208 of the image frame are encountered. The end result is an equation of a line that best fits the edge 32 or 34 that is expected near each seed pixel 86 or 88 along the signature line 36 in the image frame.

Referring now to FIG. 14 and FIGS. 18A and 18B, exemplary filtering at the block 196 will now be discussed by way of non-limiting example. As discussed above, filtering the candidate edge filter kernel lines 194, 194A, and so on depending on the iteration being performed, at the block 196 determines which of the candidate edge filter kernel lines has a maximum power level.

For each of the candidate edge filter kernel lines 194, 194A, and so on depending on the iteration being performed, a floating-point geometric coefficient map 216 of an edge detection kernel is generated. A central axis a is aligned along the candidate edge filter kernel line and is slanted at the angle of the candidate edge filter kernel line. The geometric coefficient map 216 suitably is a matrix comb of rows and columns of +1 multipliers 218 and −1 multipliers 220 oriented along the axis a.

A filtering operation suitably is executed by determining the sum of all pixel intensities at the center of the +1 multipliers 218 minus the sum of all pixel intensities at the center of the −1 multipliers 220. In the case of the opposite seed polarity, the positions of the +1 multipliers 218 and the −1 multipliers 220 are simply reversed. The candidate line which produces the maximum filter power is then forwarded to the next iteration It will be appreciated that filtering can be speeded up (that is, throttled) by performing a sparse summation. To that end and as shown in FIG. 18B, the filtering process may be speeded up by leaving out entire rows 222 of the +1 multipliers 218 and the −1 multipliers 220, or by leaving out selected components (that is, selected +1 multipliers 218 and selected −1 multipliers 220) of each row 222. It is to be understood that this reduction in coefficient number, however, will generally decrease the detection ability of the edge detection algorithm. Therefore, such reduction would work best in cases where the edges in the two-dimensional image frame are clean and well-contrasted.

Figure 19:
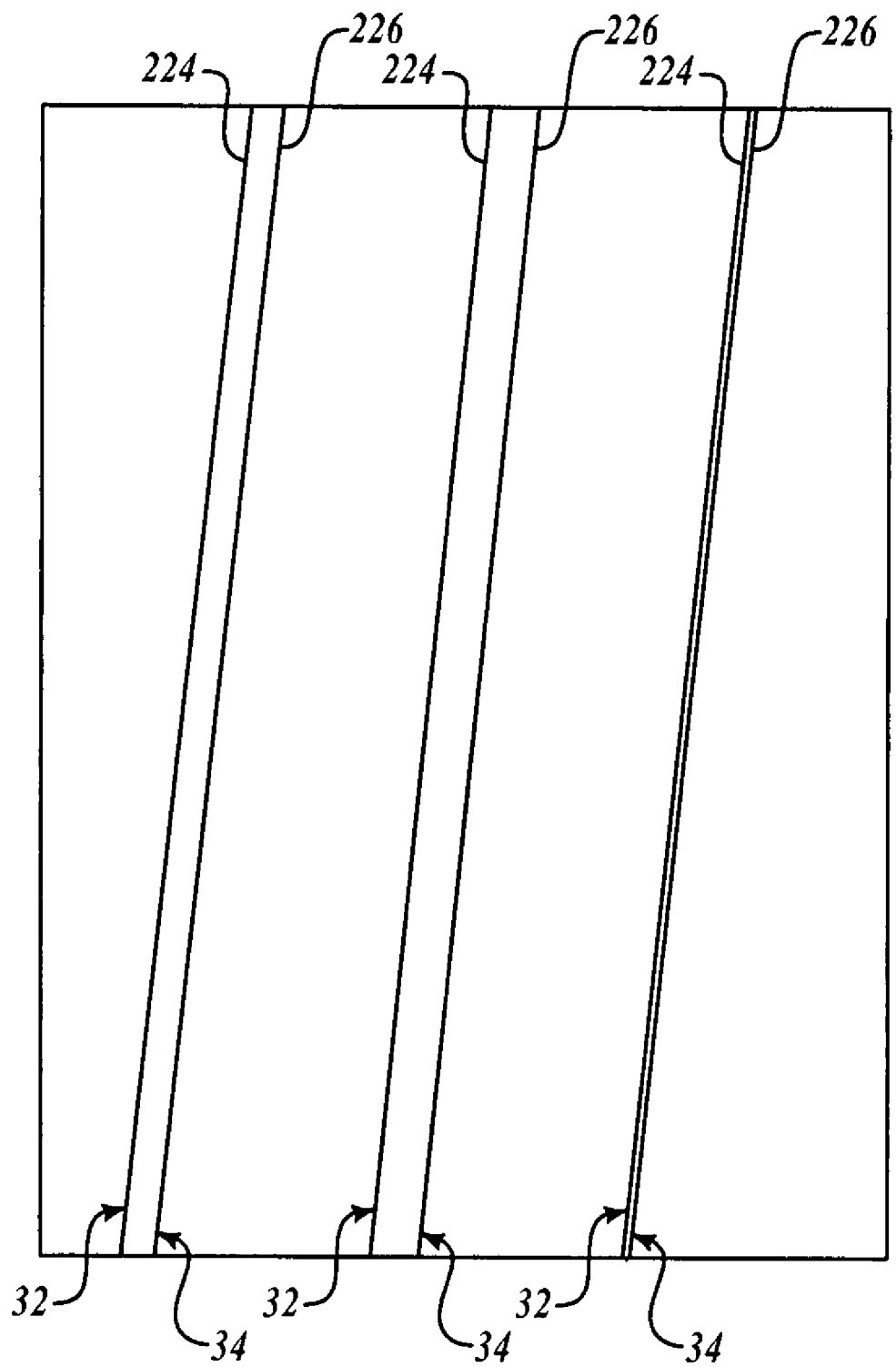
FIGS. 19 and 20 illustrate edges detected by exemplary embodiments.
Figure 20:
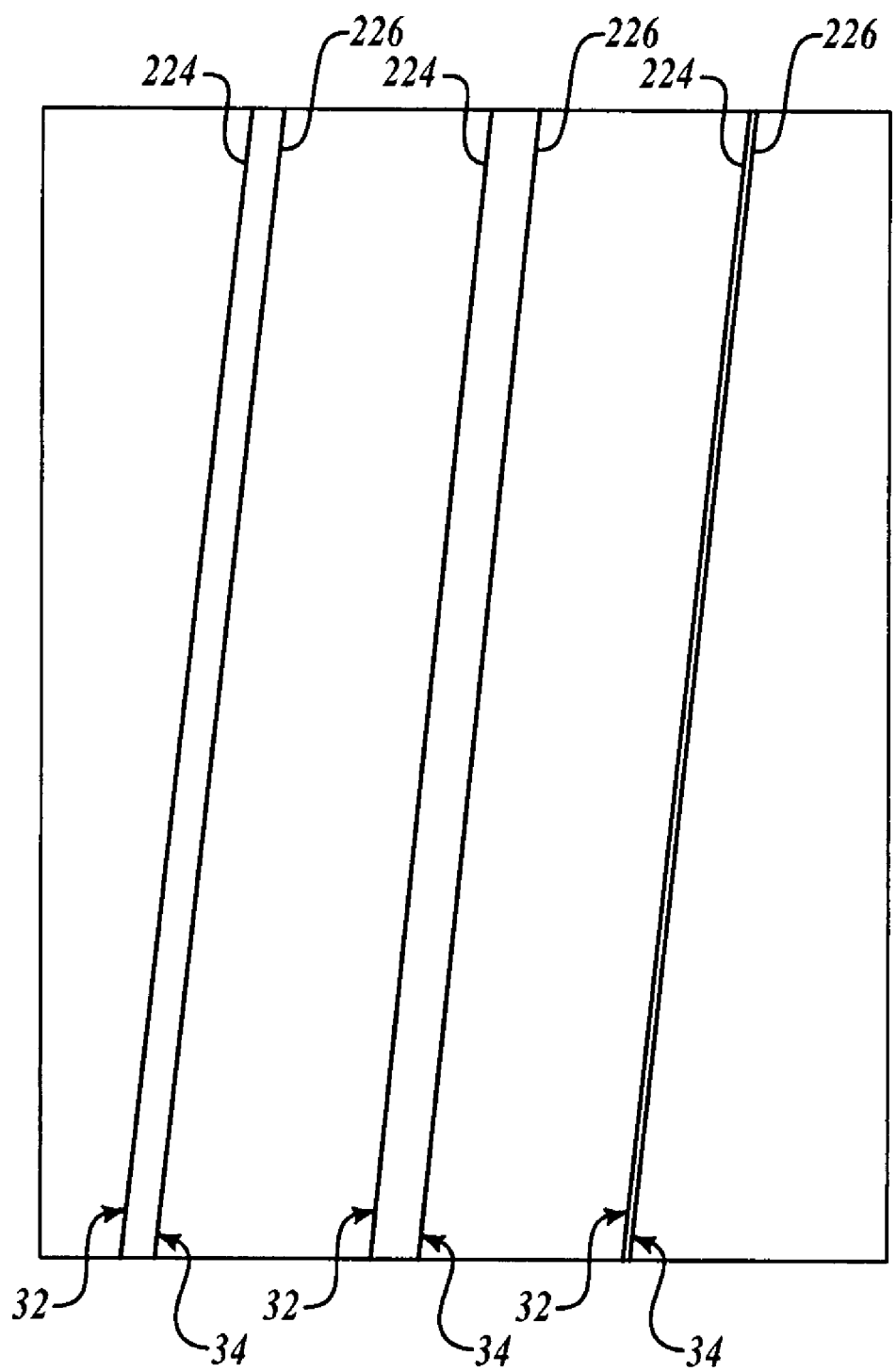

Referring now to FIGS. 19 and 20, the end result of the method 144 (FIG. 12) is an equation of a line 224 or 226 that best fits the edge 32 or 34, respectively, that is expected near each seed pixel 86 or 88 (not shown in FIGS. 19 and 20 along the signature line 36 (not shown in FIGS. 19 and 20 in the image frame. The equations for the lines 224 and 226 can be determined even if the image has been degraded, such as by rotation (FIG. 19) or by noise such as additive or multiplicative noise (FIG. 20).

While a number of exemplary embodiments and aspects have been illustrated and discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

What is claimed is:

1. A method for identifying a feature of a workpiece, the method comprising:

acquiring two-dimensional data of at least a region of a workpiece;

acquiring three-dimensional data of a portion of the region of the workpiece;

determining an estimated location of an attribute of a feature of the workpiece from the three-dimensional data; and identifying the feature by analyzing the two-dimensional data in an area surrounding the estimated location of the attribute, wherein identifying the feature includes performing a plurality of iterations of analyzing the two-dimensional data, wherein a first iteration analyzes the two-dimensional data in a first area bounded along a first dimension with a first lineal measurement and a second dimension with a second lineal measurement, and wherein a second iteration analyzes the two-dimensional data in a second area bounded along the first dimension with a third lineal measurement that is longer than the first lineal measurement and the second dimension having a fourth lineal measurement that is shorter than the second lineal measurement.

2. The method of claim 1, wherein:
the feature includes an edge; and
the attribute includes a point along a line.

3. The method of claim 1, wherein:
the feature includes a hole; and
the attribute includes a plurality of points along a circle.

4. The method of claim 1, wherein:
the feature includes a chamfered hole; and
the attribute includes a plurality of points along two concentric circles.

5. The method of claim 1, wherein acquiring the two-dimensional data includes:
illuminating at least the region of the workpiece with at least a first light source that is disposed at a first angle of incidence relative to a plane of the region; and
sensing an image of the region.

6. The method of claim 5, wherein acquiring the three-dimensional data includes:
illuminating the portion of the region of the workpiece with a second light source that is disposed at a second angle of incidence relative to the plane of the region, the second angle of incidence being greater than the first angle of incidence; and
sensing an image of the portion of the region.

7. The method of claim 6, wherein illuminating the portion of the region of the workpiece includes directing at least one laser beam onto the portion of the region of the workpiece.

8. The method of claim 7, wherein determining the estimated location of the attribute includes analyzing a plurality of steps along at least one line illuminated by the at least one laser beam.

9. A system for identifying a feature of a workpiece, the system comprising:
a first light source configured to illuminate at least a region of a workpiece;
a second light source configured to illuminate a portion of the region of the workpiece;
a sensor configured to sense an image of the region and the portion of the region; and
a processor operatively coupled to the sensor, the processor including:
a first component configured to determine an estimated location of an attribute of a feature of the workpiece from three-dimensional data regarding the portion of the region of the workpiece; and
a second component configured to identify the feature by analyzing two-dimensional data regarding the region in an area surrounding the estimated location of the attribute.

10. The system of claim 9, wherein:
the first light source is disposed at a first angle of incidence relative to a plane of the region; and
the second light source is disposed at a second angle of incidence relative to the plane of the region, the second angle of incidence being greater than the first angle of incidence.

11. The system of claim 9, wherein the first light source includes first and second lighting assemblies disposed towards first and second ends of the region, respectively.

12. The system of claim 9, wherein the second light source includes at least one laser.

13. The system of claim 9, wherein the sensor includes a camera.

14. A method of detecting an edge, the method comprising:
illuminating at least a region of a workpiece with a pair of first light sources that are disposed at a first angle of incidence relative to a plane of the region;
illuminating a portion of the region of the workpiece with a second light source that is disposed at a second angle of incidence relative to the plane of the region, the second angle of incidence being greater than the first angle of incidence;
capturing a frame of information;
determining an estimated location of a point along a line defining an edge within the workpiece from three-dimensional data from the frame of information; and
refining location of the edge by analyzing two-dimensional data from the frame of information in an area surrounding the estimated location of the point.

15. The method of claim 14, further comprising inputting into two-dimensional analysis a plurality of estimated locations of points along a plurality of lines that define a plurality of edges.

16. The method of claim 15, wherein analyzing the two-dimensional data includes formulating a plurality of candidate lines from the plurality of points at the plurality of estimated locations.

17. The method of claim 16, wherein analyzing the two-dimensional data further includes determining a median angle of the plurality of candidate lines.

18. The method of claim 17, wherein analyzing the two-dimensional data further includes comparing an angle of each candidate line with the median angle of the plurality of candidate lines.

19. The method of claim 18, wherein analyzing the two-dimensional data further includes invalidating a candidate line when its angle exceeds the median angle.

20. A memory device storing computer software program code that is executable by a processor to:
analyzing analyze three-dimensional information to determine a plurality of estimated locations of points along a plurality of lines defining a plurality of edges;
analyze two-dimensional information in a plurality of areas surrounding the estimated locations of the points to refine locations of the edges;
formulate a plurality of candidate lines from the points at the plurality of estimated locations; and
determine a median angle of the plurality of candidate lines.

21. The memory device of claim 20, wherein the computer software program code is further executable by the processor to compare an angle of each candidate line with the median angle of the plurality of candidate lines.

22. The memory device of claim 21, wherein the computer software program code is further executable by the processor to invalidate a candidate line when its angle exceeds the median angle.

23. A head assembly for performing a manufacturing operation on a workpiece, the head assembly comprising:
a tool moveable relative to a workpiece and configured to perform a manufacturing operation on the workpiece; and
a monitoring unit operatively coupled to and moveable with the tool relative to the workpiece, the monitoring unit including:
first and second lighting assemblies disposed towards first and second sides of the monitoring unit, respectively, the first and second lighting assemblies being configured to illuminate at least a region of the workpiece;
a laser assembly configured to illuminate a portion of the region of the workpiece upon which the tool has performed the manufacturing operation;
a sensor configured to sense an image of the region and the portion of the region; and
a processor operatively coupled to the sensor, the processor including:
a first component configured to determine an estimated location of an attribute of a feature of the workpiece from three-dimensional data regarding the portion of the region of the workpiece; and
a second component configured to identify the feature by analyzing two-dimensional data regarding the region in an area surrounding the estimated location of the attribute.

24. The head assembly of claim 23, wherein the tool is configured to perform an application of a composite tape onto the workpiece, and wherein the monitoring unit is configured to illuminate at least a region of the composite tape.

25. The head assembly of claim 24, wherein the tool includes:
a spindle configured to support a supply of the composite tape; and
a feed assembly configured to feed the composite tape from the supply to the workpiece, the feed assembly having a rotatable compaction roller configured to apply the composite tape onto the workpiece.

26. The head assembly of claim 23, wherein:
the first and second lighting assemblies are disposed at a first angle of incidence relative to a plane of the region; and
the laser assembly is disposed at a second angle of incidence relative to the plane of the region, the second angle of incidence being greater than the first angle of incidence.

27. The head assembly of claim 23, wherein the sensor includes a camera.

28. A system for performing a manufacturing operation on a workpiece, the system comprising:
at least one head assembly configured to perform a manufacturing operation on a workpiece, the head assembly including;
a tool moveable relative to a workpiece and configured to perform the manufacturing operation on the workpiece; and
a monitoring unit operatively coupled to and moveable with the tool relative to the workpiece, the monitoring unit including:
first and second lighting assemblies disposed towards first and second sides of the monitoring unit, respectively, the first and second lighting assemblies being configured to illuminate at least a region of the workpiece;
a laser assembly configured to illuminate a portion of the region of the workpiece upon which the tool has performed the manufacturing operation;
a sensor configured to sense an image of the region and the portion of the region; and
a processor operatively coupled to the sensor, the processor including:
a first component configured to determine an estimated location of an attribute of a feature of the workpiece from three-dimensional data regarding the portion of the region of the workpiece; and
a second component configured to identify the feature by analyzing two-dimensional data regarding the region in an area surrounding the estimated location of the attribute; and
a translation platform coupled to the at least one head assembly, the translation platform being configured to operatively position the at least one head assembly proximate the workpiece and to systematically move the at least one head assembly along a translation path proximate the workpiece.

29. The system of claim 28, wherein the tool is configured to perforin an application of a composite tape onto the workpiece, and wherein the monitoring unit is configured to illuminate at least a region of the composite tape.

30. The system of claim 29, wherein the tool includes:
a spindle configured to support a supply of the composite tape; and
a feed assembly configured to feed the composite tape from the supply to the workpiece, the feed assembly having a rotatable compaction roller configured to apply the composite tape onto the workpiece.

31. The system of claim 28, wherein:
the first and second lighting assemblies are disposed at a first angle of incidence relative to a plane of the region; and
the laser assembly is disposed at a second angle of incidence relative to the plane of the region, the second angle of incidence being greater than the first angle of incidence.

32. The system of claim 28, wherein the sensor includes a camera.

33. A method of performing a manufacturing operation on a workpiece, the method comprising:
performing a manufacturing operation on a portion of a workpiece using a tool moveable relative to the workpiece;
simultaneously with performing the manufacturing operation, translating the tool relative to the workpiece; and
simultaneously with performing the manufacturing operation, monitoring a portion of the workpiece upon which the tool has performed the manufacturing operation, wherein the monitoring includes:
acquiring two-dimensional data of at least a region of the workpiece;
acquiring three-dimensional data of a portion of the region of the workpiece;
determining an estimated location of an attribute of a feature of the workpiece from the three-dimensional data; and
identifying the feature by analyzing the two-dimensional data in an area surrounding the estimated location of the attribute.

34. The method of claim 33, wherein performing the manufacturing operation includes applying a composite tape onto the workpiece.

35. The method of claim 34, wherein performing the manufacturing operation further includes feeding the composite tape from a tape supply to a compaction roller, and wherein applying the composite tape includes compacting the composite tape onto the workpiece using the compaction roller.

36. The method of claim 33, wherein acquiring the two-dimensional data includes:
illuminating at least the region of the workpiece with first and second lighting assemblies that are disposed at a first angle of incidence relative to a plane of the region; and
sensing an image of the region.

37. The method of claim 36, wherein acquiring the three-dimensional data includes:
illuminating the portion of the region of the workpiece with a laser assembly that is disposed at a second angle of incidence relative to the plane of the region, the second angle of incidence being greater than the first angle of incidence; and
sensing an image of the portion of the region.

38. A method comprising:
acquiring two-dimensional data of at least a region of a workpiece, wherein acquiring the two-dimensional data includes:
illuminating at least the region of the workpiece with at least a first light source that is disposed at a first angle of incidence relative to a plane of the region; and
sensing an image of the region;
acquiring three-dimensional data of a portion of the region of the workpiece, wherein acquiring the three-dimensional data includes:
illuminating the portion of the region of the workpiece with a second light source that is disposed at a second angle of incidence relative to the plane of the region, the second angle of incidence being greater than the first angle of incidence; and
sensing an image of the portion of the region;
determining an estimated location of an attribute of a feature of the workpiece from the three-dimensional data; and
identifying the feature by analyzing the two-dimensional data in an area surrounding the estimated location of the attribute.

* * * * *